United States Patent [19]

Figueras

[11] 4,144,306
[45] Mar. 13, 1979

[54] ELEMENT FOR ANALYSIS OF LIQUIDS

[75] Inventor: John Figueras, Victor, N.Y.

[73] Assignee: Eastman Kodak Company, Rochester, N.Y.

[21] Appl. No.: 877,193

[22] Filed: Feb. 13, 1978

Related U.S. Application Data

[63] Continuation-in-part of Ser. No. 759,527, Jan. 14, 1977, abandoned.

[51] Int. Cl.$^2$ .................... G01N 31/14; G01N 33/16; G01N 21/06
[52] U.S. Cl. .............................. 422/56; 195/103.5 S; 23/231
[58] Field of Search ......................... 23/253 TP, 231; 195/103.5 R, 103.5 S, 103.5 A

[56] References Cited

U.S. PATENT DOCUMENTS

| | | | |
|---|---|---|---|
| 3,641,235 | 2/1972 | Weiss | 424/8 |
| 3,694,318 | 9/1972 | Klein et al. | 195/103.5 R |
| 3,888,739 | 6/1975 | Whetzel et al. | 195/103.5 S |
| 3,992,158 | 11/1976 | Pygbylowicz et al. | 23/253 TP |
| 4,042,335 | 8/1977 | Climent | 23/253 TP |

Primary Examiner—Morris O. Wolk
Assistant Examiner—Michael S. Marcus
Attorney, Agent, or Firm—Ronald P. Hilst

[57] ABSTRACT

A multilayer analytical element for the analysis of liquids, particularly small samples of biological liquids, having at least two layers including a reagent layer and a registration layer. The reagent layer contains an interactive composition including a nondiffusible material having a preformed detectable moiety, such composition being interactive in the presence of liquid containing an analyte of choice to provide a diffusible product comprising the preformed detectable moiety. The registration layer receives the diffusible product released from the reagent layer. The layers present in the analytical element are composed such that the detectable moiety released from the reagent layer or that remaining unreleased in the reagent layer can be selectively detected in the element.

In one embodiment, there is disclosed an integral element which can include a support, preferably radiation-transmissive, on which a registration layer and a reagent layer are carried. Optionally, a spreading or analyte metering layer can be provided in the element adjacent the reagent layer to facilitate delivery of a uniform concentration of analyte to the reagent layer. In a preferred embodiment of this integral element, a radiation-blocking layer, permeable to the diffusible product, can be provided in the element intervening the reagent layer and the registration layer. The radiation-blocking layer, such as an opaque reflecting layer, can enhance the detection of the preformed detectable moiety in the registration layer or in the reagent layer by reflection densitometry or other appropriate radiometric technique.

The multilayer element of the invention is particularly useful, for example, in the assay of amylase as well as a variety of other analytes.

45 Claims, 9 Drawing Figures

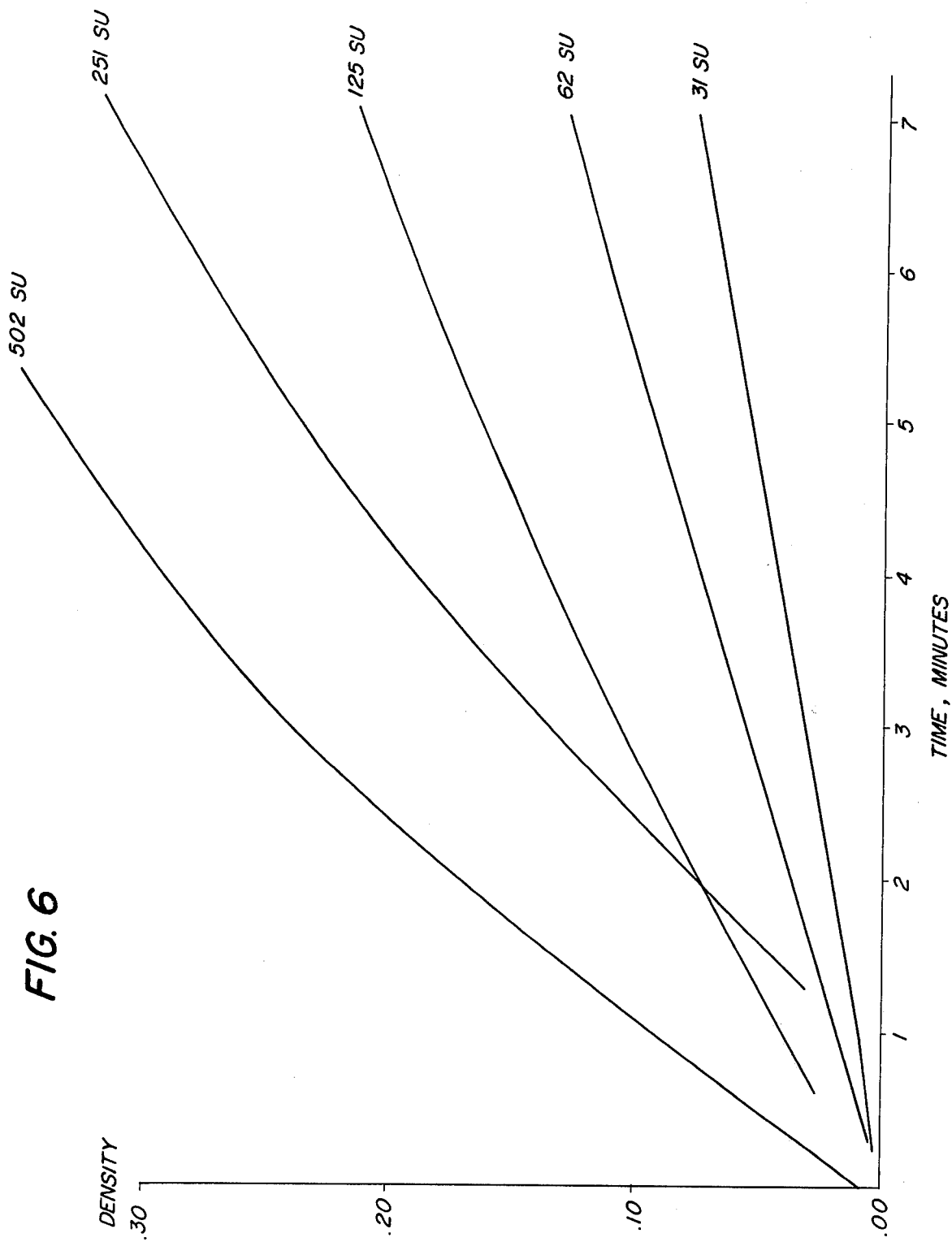

ELEMENT FOR ANALYSIS OF LIQUIDS

This application is a continuation-in-part of Figueras, U.S. Ser. No. 759,527 filed Jan. 14, 1977 now abandoned.

BACKGROUND OF THE INVENTION

1. Cross-Reference to Related Application

Reference is made to Wu, U.S. patent application Ser. No. 759,530, filed Jan. 14, 1977 and entitled "Assay for Bilirubin", now U.S. Pat. No. 4,069,016 issued Jan. 17, 1978. Certain of the multilayer analytical elements described and claimed in the aforementioned Wu application represent specific embodiments of the present invention. The invention described herein was made prior to the invention described in the cross-referenced Wu application.

2. Field of the Invention

The present invention relates to an improved multilayer analytical element for the analysis of liquids, particularly the clinical analysis of biological liquids.

BACKGROUND OF THE INVENTION

Chemical analysis of liquids such as water, foodstuffs like milk, and biological liquids is often desirable or necessary. Various elements to facilitate liquid analyses are known. Such elements have often included a reagent for a chemical substance under analysis, termed analyte herein, which reagent, upon contacting a liquid sample containing the analyte, produces formation or destruction of a colored or other type of detectable material in response to the presence of the analyte.

In certain fields, it is often required that analytical techniques yield rapid, quantitative results. Much recent development work has attempted to provide elements useful in diagnostic or clinical analysis, where testing of biological liquids including body fluids such as blood, blood serum, urine and the like, must produce a highly quantitative result, rapidly and conveniently.

In an attempt to satisfy the needs of clinical analysis work for rapid, quantitative results, a variety of solution chemical techniques, sometimes referred to in the art as "wet chemistries", have been developed for the clinical laboratory environment and have been particularly adapted for automated clinical analysis work. In such "wet chemistries" clinical reagents are dissolved or suspended in a liquid aqueous vehicle. Although useful, wet chemistry or solution assay techniques typically require analyzer equipment having intricate solution handling and transport capabilities. Analytical equipment of this "wet chemistry" variety, illustrated, for example, in U.S. Pat. No. 2,797,149 is often expensive and complex in terms of liquid handling requirements.

As an alternative to wet chemistry or solution assay techniques, various analytical elements for clinical analysis have been proposed using "dry chemistry", i.e., analytical clinical techniques wherein chemical reagents are incorporated in various substantially "dry-to-the-touch" elements such as monolayer test strips, multilayer analytical test elements, and the like. These dry chemistry analytical elements provide for the essentially dry analysis of an analyte and can offer substantial storage, handling and other convenience as compared to wet chemistry analytical techniques. To date, dry chemistry and variations of the "dry" approach have generally enjoyed only limited success and have been used primarily for qualitative and semiqualitative test purposes, usually in the form of test strips.

In wet chemistry and dry chemistry clinical analysis techniques, detection of the analyte is typically accomplished by the use of a reagent or interactive composition which, upon contact with the analyte, undergoes a detectable change, often a color change, such as by the creation or destruction of a detectable chemical species, e.g., a colored or fluorescent dye material. Determination of the presence or concentration of the analyte thus requires the formation or destruction of a detectable species which can often necessitate a series of reactions that can be difficult to control and may be subject to chemical interferences. As an example, catalase interferes with color indicating reactions based on the production of a dye using hydrogen peroxide and a dye producing material in the presence of peroxidase or other material having peroxidative activity. Further, dyes and the like detectable materials, if formed in situ during an analytical reaction or reaction sequence, must be derived from precursors having proper activity in the reactions of choice. Dyes or othr detectable materials formed from precursors having such reactivity may be difficult to measure accurately in the detection environment. Such dyes may have undesirable absorption spectra (i.e., overlapping the absorption of a component of liquid under analysis), excessive or inadequate absorption, etc., all of which can impair proper response over the desired concentration range of analyte that is to be measured.

Accordingly, it would be desirable to have analytical elements for various clinical analyses in which the production of a detectable change does not require forming or destroying the detectable species to be used as the basis for analysis. This has been accomplished to some extent in various wet chemistry or solution chemistry assay techniques. For example, in the solution assay of α-amylase there have been developed various "dyed starch" materials which, upon being dissolved or suspended in a suitable aqueous carrier, can be used as an interactive composition for the detection of α-amylase. These dyed starches typically have a preformed dye chemically attached to the starch to form the desired dyed starch. Because α-amylase is an enzyme which specifically degrades starch in biological fluids, the aforementioned dyed starches, upon admixture in a suitable liquid vehicle, provide an interactive composition for the determination of α-amylase in a particular liquid test sample. The α-amylase, if present in such liquid test sample, degrades the dyed starch so that upon separating the degraded starch from the non-degraded starch and then comparing the color density of the degraded starch to the color density of the original or of the remaining non-degraded starch, one can determine the presence or amount of α-amylase contained in the liquid test sample. A typical α-amylase assay employing the above-described "wet chemistry" is set forth in U.S. Pat. No. 3,694,318 issued Sept. 26, 1972.

The above-described wet chemistry or solution assay techniques which employ preformed detectable materials that need not be created or destroyed by interaction of the analyte can be useful. Nevertheless, these techniques suffer from the aforementioned general disadvantages of wet chemistry or solution assay techniques when it is attempted to incorporate them into automated assay systems. Such disadvantages include complex analyzer equipment, intricate solution handling and transport problems, and the like. Another problem commonly associated with wet chemistry or solution assay techniques such as those referred to above is that these techniques require termination of the interaction between analyte and colored reagent, e.g., dyed starch, followed by a separation procedure, such as centrifuging, to isolate the colored product of the interaction so that one can evaluate the color of the product without interference from the initial, identically colored reagent. Thus, these wet chemistry techniques do not easily lend themselves to rate or continuous assays where the interaction between analyte and colored reagent is allowed to continue and one evaluates the rate at which colored product of the interaction is released. This difficulty is especially troublesome in certain analyses, such as enzymatic analyses, which are particularly suited for rate assays. Therefore, it would be particularly desirable to have "dry chemistry" analytical elements which would offer the convenience and handling ease of "dry" analytical elements and which could perform continuous or rate assays, but which would employ preformed detectable materials.

To date, dry analytical test elements capable of providing quantitative analytical results, do not appear to have successfully been adapted for the incorporation or use of preformed detectable materials. Those dry elements in which preformed detectable materials have been incorporated appear to be limited to fibrous test strip elements of the type described in U.S. Pat. No. 3,641,235 dated Feb. 8, 1972. In such elements a preformed detectable species, such as a dye, is bound to an immunological reagent and the resultant dyed immunological reagent is incorporated into the fibrous layer of the element. Upon interaction of this dyed immunological reagent with the analyte to be detected in the presence of liquid eluant, some of the indicator dye is released and the eluant washes it to other regions of the same fibrous layer. Such elements appear to be effective for qualitative results only. For example, to determine the presence or absence of analyte using the aforementioned test strip, one examines the test strip visually to determine whether or not any movement or migration of dye has occurred. Moreover, the use in this test strip element of liquid eluant to wash the dye from one area of the layer to another so that dye migration can be detected also causes termination of the analyte-immunological reagent interaction. Consequently, this fibrous test strip element, like the aforementioned wet chemistry assays, is not well-suited for continuous or rate assays.

Other dry chemistry elements which have been specifically designed to provide more quantitative and precise clinical results such as the multilayer integral analytical elements described in Pryzbylowicz and Millikan, Belgian Pat. No. 801,742, dated Jan. 2, 1974, do not disclose the use therein of preformed detectable materials.

The multilayer analytical elements of the aforementioned Belgian patent provide a reagent-containing layer and an associated, isotropically-porous spreading layer that receives an applied sample and effects its distribution within the spreading layer such that a uniform apparent concentration of sample components is provided from the spreading layer to the reagent-containing layer. Preferably, such elements are substantially free from fibrous material, particularly in the spreading layer, although fibrous material could be present in minor amounts or otherwise in a manner that would not impair sample spreading, test result generation or result detection. Elements of the type described in the Belgian patent provide uniform analytical results that can be quantitative and can be measured accurately and with precision using automated spectrophotometric, fluorometric and other radiometric devices.

However, as noted above, there is no reference in the individual integral multilayer elements disclosed in Belgian Patent 801,742 to the incorporation therein of a preformed detectable material. Rather, the various specific reagents used for the detection of analytes in the Belgian patent provide for the production of analytical results by the generation and/or destruction of a detectable species within the element, for example, the generation of a colorimetrically or fluorometrically detectable species. Furthermore, there is no specific provision in the multilayer elements of the Belgian patent whereby the release of a preformed detectable material from a reagent layer thereof could be selectively detected, i.e., detected without interference from the unreleased detectable material retained in the reagent layer thereof.

Accordingly, although various analytical elements have been devised heretofore and are useful in various applications of the essentially dry analysis of liquids, such as the aforementioned fibrous test strip elements of U.S. Pat. No. 3,641,235 and the multilayer analytical elements of Belgian Pat. No. 801,742, it would be desirable to have improved "dry chemistry" analytical elements capable of providing quantitative results and of employing preformed detectable materials to achieve a quantitative and selectively detectable analytical result.

SUMMARY OF THE INVENTION

The present invention provides novel elements for analysis of liquids, such as biological liquids like blood, serum, urine, etc. The elements of the invention have at least two layers that are fluid contact under conditions of use. Elements of this invention do not require expertise in their use and, in various embodiments, they can produce quantitative analytical results without the specialized spotting or other procedures such as sample confinement, washing or removal of excess sample, that may be needed when intended for quantitative analysis. Further, as will be explained in greater detail below, the results produced by elements of this invention can be substantially consistent and free from apparent variations so that automated means of measuring electromagnetic radiation (radiometric techniques) can be used to detect such results, if necessary or desirable, with minimal risk of error.

Elements of this invention contain at least two layers including a reagent layer and a registration layer, the registration layer receiving a preformed detectable species released from the reagent layer. The layers of the multilayer elements of the invention are composed such that preformed detectable species released from the reagent layer thereof can be selectively detected in the element. This can be accomplished, for example, by structuring the elements of the invention such that the unreleased performed detectable species remaining in the reagent layer is selectively detected in the reagent layer or such that the released preformed detectable species, after migration to the registration layer, is selectively detected in the registration layer. Layers of the element are permeable to liquid under analysis.

The terms "permeable" and "permeability" are used with respect to a substance or layer to indicate its ability to be penetrated effectively by gases or liquids, including both the solvent or dispersion medium of a liquid and components carried in the medium, as by dissolution or dispersion therein. Similarly, the terms "diffusible" and "mobile" denote the capability of a material to move within a layer or analytical element by diffusion when that material is carried in liquid present in the layer or element, such as the solvent or dispersion medium of a liquid sample applied to the element. The term "component" as used herein with reference to a liquid sample refers broadly to a dissolved or dispersed ingredient of the liquid, whether the component is in its free state or is a chemical moiety that is a part of a more complex species. It will be appreciated that such ingredients can be provided in the liquid after its application to the element, such as through appropriate chemical reactions. In various cases, the component may be analyte or a precursor of analyte or a reaction product of analyte. Reaction products of components such as analytes include chemical species that are decomposition or other reaction products of a component, as well as other products derived from a component, such as reaction products formed as the result of the enzymatic activity of analyte or other component.

Reference to "fluid contact" between layers in the present elements identifies the ability of a fluid, whether liquid or gaseous, to pass in such element between superposed layers thereof. Stated in another manner, fluid contact refers to the capability of the element to permit passage of components of a fluid between the layers in fluid contact, and such capability is preferably uniform along the contact interface between fluid contacting layers. Although layers in fluid contact can be contiguous, they may also be separated by intervening layers. However, layers in the element that physically intervene layers identified as being in mutual fluid contact will also be in fluid contact and will not prevent the passage of fluid between the fluid contacting layers. Although layers can be in fluid contact prior to application of a sample to the element, it may be desirable in some circumstances to use initially spaced-apart layers and achieve fluid contact substantially at the time of sample application, as by applying a compressive force to the element.

In accordance with the present invention, the reagent layer is permeable to an applied sample and contains an interactive composition that is active in the analysis of choice. This interactive composition includes a non-diffusible material that itself includes a preformed detectable species. More particularly, the composition is interactive in the presence of liquid containing a predetermined chemical substance or analyte, i.e., the test analyte for that element, to provide or release a diffusible product that comprises the detectable species. The registration layer receives and is permeable to the diffusible product formed in the reagent layer by the above-mentioned interactive composition. In accord with a preferred embodiment of the invention, the detectable species is detected selectively in the registration layer, that is, without detection or interference from the unreleased detectable species present in other layers of the element, such as by radiometric techniques.

The terms "preformed detectable moiety", "preformed detectable species", and similar terms, as used herein refer to atoms, chemical groups (i.e., a portion of a molecule) or chemical compounds that are themselves directly detectable, for example by appropriate measurement of electromagnetic radiation such as light, radioactive emissions, etc. These terms also refer to atoms, chemical groups or chemical compounds that, although not detectable directly in the manner of choice for a particular analysis, can be rendered thusly detectable without diminishing the accuracy of the analysis, e.g., an enzyme. Desirably, such detectability can be conveniently imparted to the full amount of detectable species in the diffusible product released from the reagent layer or to the full amount of unreleased detectable species remaining in the reagent layer, without affecting the amount of diffusible product resulting from the analyte interactions which are the basis of the intended analysis. In either case, i.e., whether detected directly or indirectly, these species are present preformed in the interactive composition and are released from the reagent layer by interaction of the analyte in the presence of the interactive composition.

The present elements provide a useful analytical result, as is explained in greater detail herein, using a preformed, detectable moiety which is immobilized in a reagent layer of elements of this invention prior to the application of the liquid under analysis. Upon application of analyte-positive liquid to the element, and as a result of chemical or other interaction of the interactive composition in the presence of analyte, this preformed detectable moiety is provided as or as part of a diffusible product that can migrate by diffusion into a registration layer that is optionally carried on a radiation-transmissive support. Such supports can be radiation-transparent, i.e., transparent to electromagnetic radiation at one or more wavelengths, and this may be particularly beneficial for measurement to be made at low levels of radiation.

BRIEF DESCRIPTION OF THE DRAWINGS

In the accompanying drawings, each of FIG. 1, FIG. 2

FIG. 5 illustrates an element of the invention wherein the reagent layer and registration layer are initially spaced-apart. FIG. 4 illustrates an element of the invention havina a reagent layer strippable from the registration layer thereof.

FIGS. 6–9 are graphs illustrating certain data obtained from analytical elements in accord with the invention.

DESCRIPTION OF PREFERRED EMBODIMENTS

Figure 1:
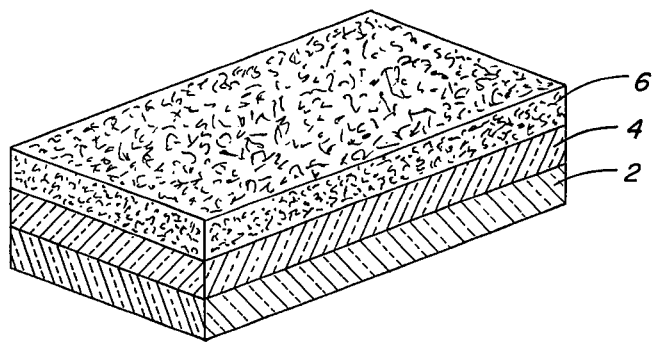
Figure 2:
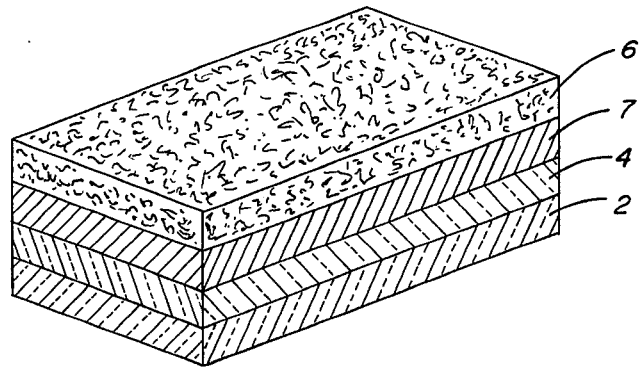
Figure 4:
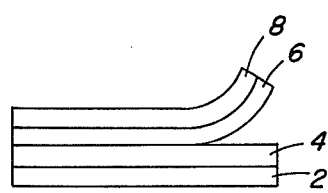
FIGS. 4 and 5 represent diagrammatic views of analytical elements in accord with other embodiments of the invention.

In accordance with the description herein and as illustrated in FIG. 1, this invention provides analytical elements that comprise:

(i) a reagent layer 6 containing an interactive composition comprising a non-diffusible material including a preformed detectable moiety, such composition being interactive in the presence of liquid containing a predetermined analyte to provide a diffusible product comprising the detectable moiety; and (ii) a registration layer 4 that receives the diffusible product, wherein layers within the element are constituted so that the detectable moiety released from the reagent layer can be detected selectively within element. For example, an opacifying material may be incorporated into the reagent layer to hide preformed detectable moiety retained in the reagent layer and to provide a background against which the detectable moiety diffused into the registration layer can be detected; or as shown in FIG. 2, a separate radiation-blocking layer may be incorporated into the element of the invention. As another example, the preformed detectable moiety may be incorporated into the interactive composition of the reagent layer in a manner such that the optical covering power thereof is reduced thereby effectively decreasing optical interference with the detectable moiety which has diffused into the registration layer. Alternatively, as illustrated in FIG. 4, the reagent layer may be strippable from the registration layer. Preferably, although not required, the registration layer is radiation-transmissive, Typically, analytical elements of the invention as illustrated in FIG. 1 have the individual layers thereof on a support 2. Preferably, although not required, the support is also radiation-transmissive. However, if the layers of the element demonstrate appropriate durability and integrity, a support is not needed.

In one preferred embodiment of the invention as illustrated in FIG. 2, an integral analytical element is provided which comprises a radiation-transmissive support 2 having thereon: (i) a reagent layer 6 that is permeable to an analyte or an analyte precursor and which contains a composition that is interactive in the presence of analyte to release a preformed, diffusible, detectable species, (ii) a radiation-blocking layer 7 that is permeable to the detectable species, and (iii) a radiation-transmissive registration layer 4 that is permeable to the detectable species and within which the detectable species can be detected. Optionally, the registration layer can include a mordant for the detectable species. The registration layer is preferably interposed between the support and the radiation-blocking layer, with the radiation-blocking layer interposed between the registration layer and the reagent layer. Also, if desired, the reagent layer is isotropically porous and preferably of substantially uniform permeability to analyte (also to an analyte precursor if appropriate) and to the diffusible, detectable species. The radiation-blocking layer, although usually not considered disruptive of the apparent concentration of detectable species provided to the radiation-blocking layer from the reagent layer, is desirably of uniform permeability to the detectable species. The registration layer is of similar permeability as regards the detectable species. Preferred radiation-blocking layers include an opacifying agent such as a pigment, a polymer in appropriate form, such as a blushed polymer, or both. In one preferred aspect of this embodiment, the radiation-blocking layer and registration layer are non-fibrous and one or both of these layers are substantially impermeable to the interactive composition contained in the reagent layer.

Figure 3:
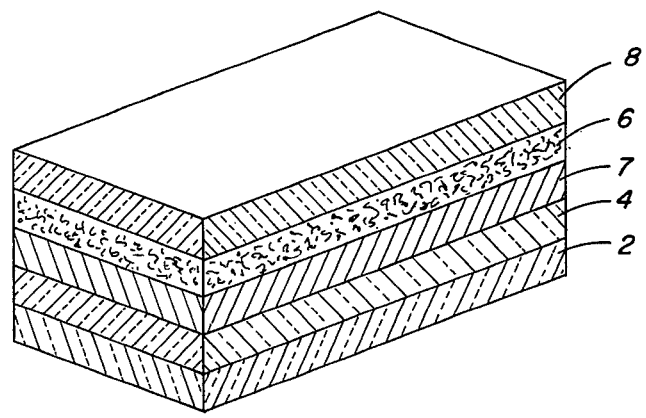
FIG. 3 is an enlarged sectional view of a preferred embodiment illustrating an integral analytical element of this invention.

In accordance with another preferred embodiment of the present invention as illustrated in FIG. 3, there is provided an integral analytical element with a support 2 having thereon a reagent layer 6, a registration layer 4 and, optionally, a radiation-blocking layer 7, all as described above with respect to the foregoing preferred embodiment. Additionally, however, there is included in elements according to this preferred embodiment a non-fibrous spreading layer 8, desirably isotropically porous and positioned in the element such that the reagent layer is interposed between the registration layer and the spreading layer. The spreading or analyte metering layer can facilitate delivery of a uniform concentration of analyte to the reagent layer. In one aspect of this embodiment, all layers are preferably non-fibrous, to enhance the quantitative analytical capability of the element. The term "non-fibrous" is used herein with respect to layers and/or materials to indicate that such layers or materials are free or substantially free from fibrous materials, that is, they do not include fibrous components to a degree that would interfere with sample spreading as discussed herein or with detection of the analytical result by radiometric means.

In accord with a further embodiment of the invention as illustrated in FIG. 4, reagent layer 6 and optional spreading layer 8 may be strippable from the registration layer 4 of the element. In such case, for example, the registration layer 4 can be carried on a radiation-transmissive or opaque support 2 and the amount of preformed, detectable species released into the registration layer can be radiometrically determined by making appropriate optical transmission or reflection measurements of the registration layer after the reagent and optional spreading layer have been stripped from the registration layer.

Figure 5:
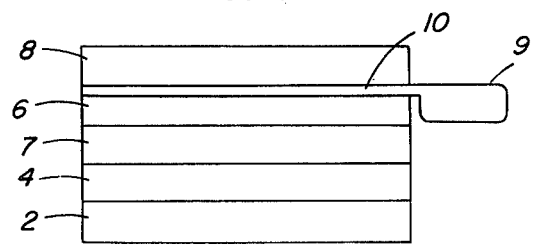

In another embodiment of the invention, some or all of the individual layers of the element are initially spaced apart from one another and, upon application of liquid test sample to the element, the element is subjected to a compressive force whereby the layers are brought into fluid contact. Such a configuration is useful where it is desired to avoid contact between individual layers of the element until the liquid test sample is applied thereto, for example, to prevent premature migration of preformed detectable species to the registration layer. Such premature migration can occur where, for example, the interactive composition containing the preformed detectable species is of relatively low molecular weight and where the element of the invention may be subjected to long-term keeping prior to its use or adverse environmental conditions such as high relative humidity ot temperature conditions during keeping. Alternatively, such a structural configuration of the element is useful as illustrated in FIG. 5 where it is desired to store a separate liquid component within the element, such as by sealing the liquid within one or more pods or compartments 9 sandwiched between or within an individual spacer layer 10 of the test element, whereby such liquid component can be introduced into the element at the time of use by applying compressive force to the element and rupturing the pod(s) or compartments in which the liquid has been stored. In FIG. 5, layers 8, 7, 4 and 2 represent a spreading layer, radiation-blocking layer, registration layer, and support, respectively as noted with respect to FIG. 3. In this regard, the use of one or more pods 9 associated with the reagent layer 6 of the element illustrated in FIG. 5 is particularly useful where the reagent layer 6 comprises a composition containing a diffusible dye moiety which is released therefrom upon interaction with analyte-positive test sample in the presence of a highly corrosive medium, either alkaline or acid. In such case, the corrosive medium, which may hav a deleterious effect when allowed to contact other layers or components of the test element for long periods of time or which may present a difficult element handling and keeping problem, can be stored within a rupturable, acid- or alkaline-impermeable pod or similar means until the element is ready for use, thereby avoiding the aforementioned undesirable effects of such corrosive materials. Because the elements of the invention can be discarded or remain sealed after use, one need not be concerned with the effects of the corrosive medium after use of the element so long as the element is properly sealed or otherwise handled to prevent unwanted leakage of the corrosive medium subsequent to rupture of container means 9 and provided that proper procedures are followed in the discard of the used element.

Reagent layers of elements according to this invention are permeable, and porous if appropriate, to at least such components of liquid under test as are active in the analysis of choice. Permeability, as intended herein, is meant to include permeability arising from porosity, ability to swell or any other characteristc. Reagent layers usually contain a matrix or carrier in which an interactive composition as described herein is distributed, i.e., dissolved or dispersed. However, if, for example, the interactive composition can itself be formed into a discrete layer, it may not be necessary for the reagent layer to contain a matrix. The choice of matrix will depend to a degree on the use for which an element is intended, i.e., qualitative, semiquantitative or quantitative analysis. Various porous, fibrous materials like papers, fleeces, felts, woven fabrics or the like, whether formed from natural or synthetic materials, have been popular in test elements and can be used. Such materials and their manner of use in analytical elements have been described, for example, in U.S. Pat. Nos. 3,802,842, 3,809,605, 3,897,214. and 3,987,214. Other porous, but nonfibrous reagent carriers that are useful include microporous polymers such as those referred to in U.S. Pat. No. 3,552,929, plastic sponge materials and porous ceramics as referred to in U.S. Pat. No. 3,554,700, granulated substances such as those referred to in U.S. Pat. No. 3,715,192, and polymeric open-cell foams as referred to in U.S. Pat. No. 3,917,453.

Still other desirable reagent carriers include gel layers permeable to applied liquid samples. One such variety of film former, described in U.S. Pat. No. 3,630,957, can provide water resistant layers that are useful in analyzing aqueous liquids. Layers prepared using these film-forming materials are not considered porous in the usual sense because, as formed, they do not exhibit void structure on the colloidal level and because they pass liquids by diffusion, rather than by capillary flow which occurs in the case of porous materials. The selection of such a permeable material in any instance will depend on the applied liquid and on the size of active components that must penetrate the reagent layer.

In a preferred aspect, the film-forming material is swellable in liquid under test. Contact of a liquid sample will cause the film-forming carrier to swell and increase its permeability to the liquid of the sample. In this way, sample penetration of the reagent layer is made more rapid as is the effective contact of sample liquid and the interactive composition distributed in the reagent layer.

Gel-formers and the like are often preferred as reagent carriers in elements intended for quantitative analysis. They are usually of a much more uniform permeability to liquids than are fibrous materials. Further, they can be transparent to light and other electromagnetic radiation, which may not be the case with fibrous carriers and other porous carriers that, although nonfibrous, can be opaque or highly refractive to incident radiation due to their void structure.

The permeability of reagent layers using a homogeneous, film-forming material as a reagent matrix can be highly uniform such that, when a homogeneous liquid is provided uniformly to a surface of the layer, identical measurements of the concentration of such fluid within the layer, but made through different regions of a surface of the layer, will usually yield substantially equal results, e.g., less than about ±10% and preferably less than about ±3-5% when measured radiometrically through a small aperture such as one of about 3-10 microns wide and 50-100 microns long. If a continuous scan is used to make the measurements, a trace magnification of about 16 can be used advantageously to expand the scale. Desirably, reagent layers exhibiting substantially uniform permeability to sample fluids are also isotropically porous. Further description of typical isotropically porous layers is provided hereinafter in connection with the description of suitable isotropically porous spreading layers.

With such uniform permeability, undesirable concentration gradients of sample components can be avoided within the layer; this is desirable to facilitate the quantitative detection of analytical results. Highly uniform permeability is not considered characteristic of layers formed from fibrous materials such as filter papers, fibrous fleeces, felts, woven fabrics, etc. It is believed that factors such as variable wicking action within fibrous material can effect the formation therein, and also in fluid contacting layers composed of such fibrous materials, of various apparent concentrations of permeable liquid components. Accordingly, such carriers are considered most useful for qualitative tests.

Knowing the solvent medium of liquid under test, the choice of an appropriate film former as a reagent layer matrix will be apparent to one skilled in the solubility properties of materials. As an example, cellulose acetate of relatively low acetylation or cellulose nitrate of relatively low nitration may be useful in the case of liquids having lower alkanols as the solvent medium.

In many cases the solvent medium may be fully or effectively aqueous. An especially important group of aqueous liquids is biological liquids, such as blood plasma, serum or urine. For analysis of biological, biochemical and other aqueous liquids, hydrophilic (i.e., water wettable) film formers are especially useful as reagent carriers in preparing reagent layers. Such hydrophilic reagent carriers may also be swellable in water or other aqueous medium of a liquid under test. Desirable hydrophilic materials include naturally occurring hydrophilic colloids like gelatin; polysaccharides such as gum arabic, agar-agar and agarose; cellulose, etc., as well as derivatives thereof, and also synthetic substances such as water-soluble polyvinyl compounds like poly(vinyl alcohol) and poly(vinyl pyrrolidone), acrylamide polymers, etc.

In a reagent layer of the present elements there is provided an interactive composition that contains a nondiffusible material including a preformed detectable moiety. Depending on the nature of the interactive composition, which can also be termed a reagent composition, it may be the sole component of the reagent layer or it may be distributed together with other necessary or desirable reactants, in a carrier such as those described previously herein.

As set forth hereinabove, the interactive composition present in the reagent layer of the elements of the invention represents a composition which interacts, chemically or physically, in the presence of liquid containing a predetermined analyte, i.e., the test analyte for that element, to provide a diffusible reaction product that comprises the preformed detectable moiety. The interactive composition may be directly interactive with the test analyte, or it may be interactive with a decomposition or reaction product of the test analyte. This preformed detectable moiety of the interactive composition represents a material capable of detection, such as by radiometric or other means. Accordingly, based upon the selective detection of this material, one can analytically determine the presence or concentration of analyte in the particular liquid under analysis.

The interactive composition present in the reagent layer of the elements of the invention is an initially nondiffusible composition which can be rendered diffusible or contains a diffusible, detectable moiety. Typically, the diffusible, detectable moiety of an interactive composition is chemically or physically bound to a nondiffusible moiety of such interactive composition. In such case, upon application of analyte-positive liquid to the element, a chemical or other interaction of the interactive composition in the presence of the analyte-positive liquid occurs to release from the reagent layer an amount of the preformed diffusible, detectable moiety which can be related to the presence or concentration of analyte in the liquid test sample under analysis.

The specific composition of the interactive compositions employed in the elements of the present invention can vary considerably depending upon the particular analyte-containing liquid applied to the element and on the particular detection means used to analyze for the presence of the diffusible detectable moiety. It will further be appreciated that for any given analyte-containing liquid, there can be several different kinds of interactive compositions useful in the present invention depending upon the desired relase mechanism for the diffusible detectable moiety, i.e., the particular chemical or other interaction between the interactive composition and the analyte used to effect release of the diffusible detectable moiety.

To illustrate one aspect of the possible modifications which can be made in interactive compositions useful in the present invention, it is noted that the diffusible detectable moiety contained in the interactive composition can represent any one of a variety of different materials. In accord with a preferred embodiment of the invention, the detectable moiety represents a material which is directly detectable by radiometric means. As used herein the term "radiometric means" is defined to include any one of various analytical sensing means which employs radiation to provide an analytical result.

A partial listing of various typical detectable moieties which are directly detectable by radiometric means includes (a) colorimetrically detectable moieties, such as colorants (i.e. a dye or pigment) which have extinction coefficients or absorption spectra that can be used to determine their presence or concentration using conventional colorimetric detection devices; and (b) radiation emissive materials such as fluorescent materials, e.g. a fluorescent probe, which can be detected by a device capable of sensing radiation emitted from the materials.

Other types of radiation emissive materials, of course, can also be used as the diffusible detectable moiety contained in an interactive composition used in the invention. For example, a phosphorescent moiety or a radioactively tagged moiety may be employed such that upon treating an interactive composition containing such a detectable moiety with the particular analyte selected for testing, there is released an amount of, for example, the radioactively tagged diffusible moiety. This radioactive moiety can move into the registration layer of the element of the present invention where it is detectable by virtue of its characteristic radioactive emission.

The use of radiation emissive tags is especially useful in preparing interactive compositions composed of a tagged antigen-antibody complex which is non-diffusible and is contained in a reagent layer of a suitable element of the invention. In the presence of the appropriate analyte contained in the liquid test sample, the tagged member (i.e., either tagged antigen or tagged antibody) of the antigen-antibody complex contained in the reagent layer is displaced by an amount of the untagged member (i.e., either antigen or antibody) contained in the liquid test sample. The tagged member which has been displaced then migrates to the registration layer where it is detected by virtue of its characteristic emission. Based on the amount of tagged member detected in the registration layer, one can determine the amount of untagged member in the original liquid sample.

The above-described use of tagged or labelled antigen-antibody complexes in a recognized laboratory analysis technique. However, heretofore it is believed not to have been used in analytical elements such as provided in accord with the present invention. Elements of the present invention which employ such complexes as interactive compositions are especially appropriate in immunoassay analyses wherein the tagged antigen-antibody complex serves as a substrate for the particular antigen or antibody contained in the liquid sample under analysis. Such displacement reactions and various antigen-antibody complexes are described for example in U.S. Pat. No. 3,880,934.

In addition to the above-described moieties which are directly detectable by radiometric means, the term "preformed detectable moiety", as explained earlier herein, also includes various preformed materials which although not directly detectable can be rendered thusly detectable without diminishing the accuracy of the analysis. In accord with a preferred embodiment, such detectability is imparted to the full amount of the detectable moiety contained in the diffusible product of the interactive composition which migrates out of the reagent layer and into the registration layer and, in addtion, such detectability is imparted without affecting the amount of such diffusible product. Examples of such preformed detectable moieties include fluorescent probe materials which is their free state exhibit a low level of fluorescence, but which when bound to a suitable carrier are highly fluorescent; enzyme labelled antigens which diffuse into a registration layer containing a substrate material for such enzyme label, the substrate material comprising, for example, a reaction mixture which is catalyzed by such enzyme label to yield a directly detectable reaction product, e.g., a dye.

From the above discussion it will be apparent that a variety of different detectable materials can be used as the detectable species contained in the reagent layer of the elements of the present invention. These detectable materials include such materials as various preformed dyes which are detected by their characteristic absorption spectrum or various emissive materials such as fluorescent probes or phosphorescent and radioactive materials which are detectable by virtue of their characteristic emission spectrum. Specific representaive dyes and fluorescent materials are more particularly illustrated hereinafter; representative phosphorescent and radioactive materials include such well known materials as various phosphors such as substituted coumarins, fluoresceins, rhodamine dyes, etc. and various radioactive groupings such as carbon 14 or heavy hydrogen (tritium).

Apart from the specific materials and properties of such materials which are used as the preformed detectable moiety of the interactive compositions employed in the present invention, it will be appreciated that a variety of means may be employed to provide release of the diffusible detectable moiety from the interactive composition. As will be apparent, the release of the detectable moiety from the nondiffusible interactive composition will depend upon the particulr means whereby the preformed diffusible detectable moiety is attached to the reagent composition and the mechanism by which it is released. A partial listing of representative release mechanisms, together with specific examples of interactive compositions which employ such mechanisms, for detachment of the diffusible detectable moiety from the interactive composition is provided in the following discussion:

HYDROLYTIC RELEASE

Hydrolytic release, as its name implies, relates to and includes those mechanisms whereby the preformed diffusible detectable species is released from the interactive composition as a result of a hydrolysis reaction. A typical example of one such hydrolytic release mechanism, which also constitutes a highly preferred embodiment of the present invention, may be illustrated by reference to an element of the present invention which contains a reagent composition suitable for determining the α-amylase content of a biological sample, such as human serum. In such case the reagent or interactive composition, which serves as a substrate for the amylase contained in the particular sample to be analyzed, is composed of starch which has a preformed detectable species such as a dye chemically bonded to individual repeating glucose units of the starch. As is known, the enzyme α-amylase causes the catalytic hydrolysis of starch which results in the breakdown of the starch into a series of lower molecular weight polysaccharide units. This breakdown occurs as the result of the hydrolysis of the α-1,4 linkages of the amylose and amylopectic fractions, these fractions being the principal components of starch.

In accord with the present invention, it has been found that by incorporating the above-described starch substrate containing a preformed detectable moiety into the reagent layer of the elements of the invention, one can obtain a resultant interactive composition which is essentially nondiffusible throughout the reagent layer in the presence of an α-amylase-free fluid sample. However, in the presence of a sample which contains α-amylase, there is produced the characteristic catalytic hydrolytic breakdown of the starch substrate. As a consequence, there is released from the starch interactive composition low molecular weight polysaccharide units which, by virtue of their low molecular weight, are diffusible and migrate in the presence of the aqueous sample through the reagent layer into the registration layer. The presence of low molecular weight polysaccharide units which so diffuse into the registration layer is determined in accord with the present invention by monitoring the presence of the detectable moiety which appears in the registration layer. Because the detectable moiety is chemically bonded to the individual low molecular weight polysaccharide units, such monitoring permits one to determine the presence of these units in the registration layer. The presence of these units in the registration layer thus provides a convenient test for the presence or absence of α-amylase in the initial serum sample.

The selection and preparation of a particular nondiffusible starch substrate containing a detectable moiety for use as an interactive composition in accord with the present invention can be made using a variety of starches and detectable materials. Broadly, the particular detectable moiety employed can be any one of those described hereinabove including radioactive tags, colorimetrically detectable materials such as dyes, fluorescent dyes, and the like. Of course, the particular moiety selected must bind, either physically or by a chemical linkage, to the individual repeating saccharide units of the starch molecule. And, preferably, the detectable moiety should be physically and chemically inert with respect to various components of the liquid sample to be tested other than α-amylase.

In accord with the present invention, good results using the above-described element for the analysis of α-amylase can be obtained by employing as the nondiffusible interactive composition materials which are colorimetrically detectable, for example, starches complexed with conventional colorimetrically detectable dyes which are known to be capable of complexing with starches, for example, the various halogenated cyanuric based dyes such as the chlorotriazine dyes [commercially available, for example, from Ciba-Geigy Co., Inc. under the tradenames Cibracon ® Brilliant Orange G.P. (Reactive Orange 5) and Cibracon ® Brilliant Blue F3GA (Reactive Blue 2)]; and the like. The preparation of statch complexes containing the above-described detectable groups is well known and detailed discussion thereof is unnecessary herein. However, for purposes of reference, one can refer to U.S. Pat. Nos. 3,579,322 issued Aug. 3, 1971 and 3,694,318 issued Sept. 26, 1972 for a description of various starch-halogenated cyanuric based dye complexes.

Useful results have also been obtained in accord with the invention using a nondiffusible fluorescent starch complex as the interactive composition, the hydrolytic cleavage of which is catalyzed by α-amylase. One good example of a fluorescently labelled starch complex is that obtained from the reaction of amylase with isatoic anhydride, a known fluorescent species. When this reaction is carried out under the appropriate conditions, e.g., using a pyridine catalyst and carrying out the reaction in the presence of dimethyl sulfoxide solvent, it has been found that one can obtain a highly fluorescent starch reaction product in which a relatively large number of individual-repeating glucose units of the starch polymer have been esterified and converted to anthranilate units. The chemical equation for this reaction is as follows:

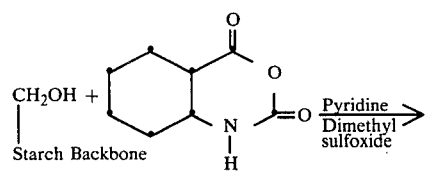

-continued

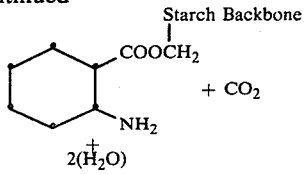

The resultant fluorescent starch exhibits a high degree of fluorescence because of the relatively large number of glucose units which are converted to anthranilate units. In particular one obtains a starch optimally having one anthranilate unit per six glucose units.

As will be appreciated, the particular detectable moiety for use in the above-described assay for α-amylase will depend, in large part, on the particular properties of the resultant amylose starch-detectable moiety complex which is desired for use as an interactive composition in the invention. For example, one can employ a soluble or insoluble starch-detectable moiety complex for use in the invention, the solubility thereof having reference to solubility in an aqueous medium as measured at 22° C. and at a pH of 7.0. One water-insoluble starch-detectable moiety complex useful as an interactive composition in accord with the invention is that described in the above-noted U.S. Pat. No. 3,694,318. Alternatively, examples of various water-soluble, starch-detectable moiety complexes useful in the invention include the water-soluble complexes as described in U.S. Pat. No. 3,597,322 noted above. Other similar water soluble dye-starch complexes are described in U.S. Pat. Nos. 3,705,149 issued Dec. 5, 1972 and 3,679,661 issued July 25, 1972.

The starch which is used to prepare the above-described starch complexes for use in the invention can be obtained from a variety of sources including starch obtained from potato, corn, tapioca, wheat, rice, sweet potato or other sources, and starch fractions. Both water-soluble and water-insoluble starch may be used to prepare the above-described starch-detectable moiety interactive compositions. The resultant starch-containing interactive composition can be conveniently rendered nondiffusible from the reagent layer of the elements of the invention by incorporating the composition into a reagent layer having a pore size effective to prevent passage therethrough of the unhydrolyzed starch-detectable moiety interactive composition and effective to permit passage of the hydrolyzed, lower molecular weight starch-detectable moiety products. Alternatively, in accord with a preferred embodiment of the invention, the unhydrolyzed starch-detectable moiety interactive composition can be incorporated into a reagent layer which, in turn, is coated over an optional radiation-blocking layer and a registration layer (see FIG. 2 described above). In this embodiment, the pore size of the underlying registration and optional radiation-blocking layers is selected so that these layers are substantially impermeable to the unhydrolyzed starch-detectable moiety, but permeable to the hydrolyzed, lower molecular weight starch-detectable moiety products. As will be appreciated, the pore size of the reagent layer, radiation-blocking layer, and/or registration layer of a given element of the invention for the detection of amylase will depend on the molecular size of the particular unhydrolyzed starch interactive compositions and its hydrolysis reaction products which are selected for use.

DISPLACEMENT RELEASE

Release of the preformed, detectable moiety contained in the interactive composition of the reagent layer in the element of the present invention can also be accomplished through a displacement mechanism. In accord with this method of release the detectable moiety of the interactive composition is physically or chemically bound to an appropriate nondiffusible carrier, for example, a nondiffusible substrate for the analyte contained in the test samples applied to the elements of the invention for analysis. In such case as a result of a chemical or physical interaction of the analyte contained in the test sample with the nondiffusible substrate of the interactive composition, the analyte displaces or causes to displace a portion of the detectable moiety which is bound to the nondiffusible substrate; and the resultant product which is composed of diffusible detectable moiety diffuses or migrates into the registration layer of the element of the present invention where the presence and/or amount of detectable moiety contained therein can be determined. Such displacement release mechanisms are known in the art and have found application, for example, in various immunoassay techniques.

In addition, displacement release mechanisms are useful in other types of assays. For instance, elements of the present invention can be used to provide an assay for bilirubin. This can be accomplished by employing as the interactive composition a bilirubin-active complex composed of, e.g., a preformed detectable ligand bound to a carrier such as albumin. When such conplexes are contacted with bilirubin, bilirubin competes with the detectable ligand for binding sites on the albumin carrier thereby causing detectable ligand to be released. Upon diffusion of the ligand from the reagent layer of the element into the registration layer, one can determine the presence or amount of bilirubin in the original test sample by evaluating the amount of diffusible ligand released from the bilirubin-active complex. This analytical method for bilirubin determination, as noted above, is based upon the competitive displacement of a preformed detectable moiety, e.g., a fluorescent probe, from a fluorescent probe-albumin interactive composition which serves as a substrate for the bilirubin analyte. Particularly useful bilirubin-active complexes for analysis of bilirubin by the above-described technique are described in Wu, U.S. Pat. No. 4,069,016 issued Jan. 17, 1978. A representative example taken from said patent is incorporated in the working examples appended to the present specification to demonstrate the scope of the present invention and particularly the utility of displacement release mechanism in elements of the present invention.

OXIDATIVE AND REDUCTIVE RELEASE

These release mechanisms, as the name implies, employ oxidation or reduction of the nondiffusible interactive composition in the presence of analyte to facilitate release of the diffusible preformed detectable moiety from the reagent layer of the element of the invention. A wide variety of such release mechanisms are known, for example, in the field of photographic chemistry where they have been employed, for instance, in silver halide diffusion transfer image forming processes, and can be adapted for use in the present invention.

Oxidative or reductive release can occur, in some cases, directly as a consequence of oxidizing or reducing the interactive composition contained in the reagent layer. For example, one can select as the analyte substrate a nondiffusible interactive composition having a detectable moiety chemically linked thereto, which linkage upon oxidation or reduction is cleaved to release the diffusible detectable moiety. Alternatively, one can select as the interactive composition a material which is nondiffusible because of its large molecular size or particular molecular configuration, which size or configuration is altered by oxidation or reduction to form a diffusible species being or containing the detectable moiety. For example, one can select as the nondiffusible substrate a high molecular weight material which upon oxidation or reduction is degraded or broken up to form a number of smaller chemical units of much lower molecular weight which are thereby rendered diffusible. Or, one can choose as the interactive composition a material which contains a particular group rendering the material nondiffusible, sometimes referred to as a "ballast" group, which group is cleaved from the interactive composition or otherwise converted (e.g., such as by converting an insolubilizing group into a soluble species) as a consequence of oxidation or reduction, thereby yielding a resultant diffusible product containing the detectable moiety.

As discussed above, "direct" oxidative or reductive release mechanisms are employed by selection of an appropriate interactive composition which, in the presence of the analyte to be detected, is oxidized or reduced to provide directly a resultant diffusible material which contains the detectable moiety. Interactive compositions which operate according to such a "direct" release mechanism could, for example, include the leuco form ring closure compounds such as described in U.S. Pat. No. 3,443,940, issued May 13, 1969. Such compounds are initially nondiffusible due to the presence of an appropriate ballast group and contain a dye chemically linked thereto. Upon oxidation of these leuco form ring closure compounds, the chemical link which serves as the point of attachment for the dye undergoes a ring closure reaction and releases the dye.

In addition to the above-described "direct" oxidative or reductive release mechanisms, a variety of release mechanisms described herein as "indirect" oxidative or reductive release mechanisms may be employed. In these situations, as in the so-called "direct" mechanisms noted above, release of the detectable moiety from the interactive composition is facilitated by oxidation or reduction of the interactive composition. However, in these release mechanisms one or more additional interactions typically are carried out prior to release of the detectable moiety, e.g. a dye. Again, a variety of such indirect oxidative or reductive release chemistries have been described in various silver halide photographic patent publications, and in accord with the present invention these release chemistries can be adapted for use as the release means associated with the interactive compositions described in the present specification.

For example, many of such indirect oxidative or reductive release mechanisms can be adapted for use in the present invention by employing an immobile or nondiffusible interactive composition having associated therewith a separate oxidizable or reducible co-reactant, such as a photographic developing agent, a photographic coupling agent, and the like. Upon oxidation or reduction of such co-reactant, depending upon the particular co-reactant and its desired oxidation state, the thus oxidized or reduced co-reactant interacts with the immobile species of the interactive composition to split off (e.g., by a coupling or cross-oxidation reaction) a diffusible detectable moiety such as a dye. One example of such a dye release chemistry is described in U.S. Pat. No. 3,628,952 issued Dec. 21, 1971. This patent describes certain ballasted dye-containing sulfonylhydrazone compounds which interact with the oxidized form of a developing agent, such as catechol, and thereby split off a diffusible dye-containing moiety from the ballasted starting material.

Other indirect oxidative or reductive dye release chemistries which rely upon a release mechanism somewhat similar to that described in U.S. Pat. No. 3,628,952 noted above include various coupling release chemistries such as those described in U.S. Pat. Nos. 3,227,550 and 3,476,563. In these patents a photographic coupler, which has chemically attached thereto a ballast group to render the coupler nondiffusible, is joined at the coupling site thereof through a chemical linkage to a dye which is chemically attached to a solubilizing group. Such couplers undergo a coupling reaction with conventional primary aromatic amine color photographic developers (which have themselves been oxidized) to couple off or split off the ballasted coupling group and to thus release the dye which, due to the solubilizing group(s) attached thereto, is diffusible, for example, in an alkaline medium. Still other dye release chemistries which produce diffusible dye through a coupling release mechanism are described in German OLS 2,415,125.

Yet another type of indirect dye release chemistry which employs a chemical coupling reaction between color photographic developer which has been oxidized and a ballasted dye-providing reactant is that relating to certain additional ring closure compounds described in the above referred to U.S. Pat. No. 3,443,940 and U.S. Pat. No. 3,443,939, issued May 13, 1969. These patents describe certain ballasted phenolic compounds having a dye attached to the phenolic nuclei thereof through a chemical linkage. Upon interaction with an oxidized primary aromatic amine color developer co-reactant, these ballasted phenolic compounds couple to the oxidized color developer. In the chemical compound which is the product of this reaction, the residue of the primary amino color developer and the chemical linkage joining the dye moiety to the phenolic nuclei undergo a spontaneous ring closure reaction to split off and release diffusible dye.

An additional indirect oxidative or reductive dye release chemistry which may be adapted for use in the interactive compositions of the analytical elements of the present invention are those release mechanisms such as described in U.S. Pat. No. 3,728,113 and U.S. published application B351,673 published Jan. 28, 1975. These publications describe a dye release mechanism which employs direct oxidation of an initially immobile dye to yield an oxidized form thereof which, in the presence of an alkaline medium, hydrolyzes to cleave off a diffusible dye. For example, U.S. Pat. No. 3,728,113 issued Apr. 17, 1973, describes certain ballasted hydroquinone compounds having a dye bonded thereto through a suitable chemical linkage. Upon oxidation of such compound, the compound is converted to the quinoidal form thereof which, in the presence of an alkaline medium, hydrolyticly cleaves to release diffusible dye. In published U.S. application B351,673 certain nondiffusible phenols or anilines are described which contain a dye chemically attached to the phenolic nuclei thereof through a linking group such as a sulfonamido group. These nondiffusible compounds, upon oxidation, are converted to the quinoidal form thereof, and in the presence of an alkaline medium such quinoidal materials hydrolytically cleave to release a diffusible dye.

Similar ballasted dye-providing compounds which undergo an indirect oxidative reaction, followed by a hydrolytic cleavage of a dye are described on pages 68 to 74 of the November, 1976, issue of *Research Disclosure* (Item 15157), and in German OLS 2,402,664 and 2,505,248.

A further group of indirect oxidative or reductive release mechanisms which employ oxidation of an initially immobile or ballasted dye-containing carrier followed by hydrolysis of the oxidized product to release a dye or other detectable species is exemplified by the various hydroquinone dye-releasing compounds illustrated, for example, in U.S. Pat. No. 3,725,062 issued Apr. 3, 1973. These compounds consist of a ballasted hydroquinone nuclei to which are chemically linked a dye or other such detectable moiety. Upon oxidation, the hydroquinone nuclei are converted to the quinoidal form thereof which, in the presence of an alkaline medium, splits off the dye moiety. Another such indirect oxidative release mechanism is illustrated in Canadian Pat. No. 602,607. In this patent there are described compounds containing ballasted phenylene diamine nuclei having a diffusible dye chemically linked thereto through one of the maino substituents. Upon oxidation of these compounds, deamination of the diamino nuclei occurs at the site of the amino substituent which links the dye to the nuclei. In the presence of an alkaline medium, the diffusible dye is then released.

Another release mechanism generally similar to certain of those referred to above, but which employs a reductive, rather than an oxidative release mechanism, is described in U.S. Pat. No. 3,185,567, issued May 25, 1965. In this patent there are described certain compounds having a preformed detectable moiety, e.g., a dye, bonded to a substance, such as a quinone compound, which is initially insoluble and immobile in the presence of an alkaline medium, but which upon being reduced by an appropriate reducing agent or photographic developing agent, e.g., toluhydroquinone, become soluble and mobile in alkaline medium.

As is apparent, many of the above-described release mechanisms require the presence of an alkaline medium to facilitate release of the preformed detectable moiety. In such cases, it will be appreciated that analytical elements having a structural configuration similar to that illustrated in FIG. 5 can be especially useful because these elements are particularly adapted for use with alkaline materials, even highly alkaline liquids having a pH in excess of 13, without presenting any particular handling problem to an operator or mechanical test device which contacts elements containing such highly alkaline media.

To facilitate the detection of any preformed, diffusible detectable species which is released from the reagent layer of an element of the invention, the elements of this invention include a registration layer to receive any such released detectable species from a reagent layer. Such a registration layer is permeable to preformed detectable species in the element and is in fluid contact with a reagent layer, at least under conditions of use. Preferably, the registration layer is radiation-transmissive. The registration layer may be separated from reagent layer(s) by a radiation-blocking layer, such as a reflecting and/or opaque layer, to facilitate result detection by various radiometric techniques. The registration layer, which is also desirably swellable in liquid under analysis, can include hydrophilic colloids such as those useful in reagent layers and is preferably non-fibrous. When a reagent layer is fibrous, non-fibrous radiation-blocking and registration layers in association therewith improve the apparent uniformity of an analytical result produced in such a reagent layer.

Where the detectable species released from a reagent layer of the element is a dye or other mordantable material, the registration layer may contain a mordant, such as those described as useful image dye mordants in color photographic films and papers. Exemplary mordants are materials including vinylpyridine compounds such as poly-4-vinylpyridine, the 2-vinyl pyridine polymer metho-p-toluene sulfonate and similar compounds described in U.S. Pat. No. 2,498,430 issued Oct. 11, 1949, and cetyl trimethylammonium bromide.

In accord with a preferred embodiment of the invention, it has been found particularly useful to incorporate in the registration layer a polymeric mordant such as described in British Pat. No. 1,261,925; U.S. Pat. No. 3,625,694; 3,709,690; 3,773,509; 3,859,096; 3,898,088 and 3,958,995. Particularly useful such polymeric mordants are those materials having in the polymer chain monomeric units of the formula

I.

wherein A represents an organo group, such as an alkylene group, forming a portion of the polymer backbone; Q represents a chemical bond or an organo group linking $M^{\oplus}$ to A; $M^{\oplus}$ represents a quaternary ammonium or phoshonium group and $X^{\ominus}$ represents an anion. The preferred polymeric mordants of Formula I above have been found particularly useful in analytical elements of the invention which employ a dye as the preformed diffusible, detectable moiety released from the interactive composition contained in the reagent layer. For example, such mordants have been found to be useful in elements for the assay of α-amylase wherein the detectable moiety comprises a diffusible low molecular weight polysaccharide having bonded thereto a halogenated cyanuric based dye.

As mentioned previously, elements of this invention can include a radiation-blocking layer, preferably interposed between a reagent layer and the registration layer. Radiation-blocking layers are permeable to the preformed detectable species in the element and serve to inhibit passage of electromagnetic radiation, such as at the wavelength or wavelengths used for detection. Using such a layer, color or other potential interferents to result detection can be masked from the registration layer or the reagent layer, depending upon whether released or unreleased detectable species is monitored, respectively. Such layers include an opacifying agent that, by virtue of its absorbance, reflectance or the like, provides a radiation inhibiting effect when incorporated into the layer. In one aspect, the radiation-blocking layer can include a matrix containing an opacifying agent, such as a pigment like carbon or other inorganic pigment such as a metal salt like titanium dioxide, zinc oxide, barium sulfate, etc. Blushed polymers, which are generally reflective in nature, can comprise the opacifying agent and layers of such blushed polymers as are useful in spreading layers (which are described hereinafter) can be used also as radiation-blocking layers. It will be appreciated that if a microporous, blushed polymer layer is used as a radiation-blocking layer, such layer can also serve as a filtering layer. Such a layer is useful in the event that the registration layer is permeable to filterable substances which could impair result detection in the registration layer if allowed to enter the registration layer from the reagent layer.

In one preferred aspect, blushed polymer layers can also incorporate a reflective inorganic pigment, such as the highly reflective pigments mentioned elsewhere herein, to enhance reflectivity and/or spreading (as described hereinafter with respect to spreading layers). The amount of pigment that can be included in a layer together with blushed polymer is highly variable, and amounts of from about 5 percent by weight to about 1,000 percent by weight of pigment based on the weight of blushed polymer are preferred, with a pigment concentration of from about 100 weight percent to about 600 weight percent pigment based on the blushed polymer being most preferred.

As mentioned previously, an element of this invention can optionally include a spreading layer, such as is described, in detail, in Przybylowicz and Millikan, U.S. Pat. No. 3,992,158, issued Nov. 16, 1976. The spreading layer is a layer that can accept a liquid sample, whether applied directly to the spreading layer or provided to it from a layer or layers in fluid contact with the spreading layer, and within which the solvent or dispersion medium of the sample and at least one solute, dispersoid (constituent of the dispersed or internal phase) or reaction product of solute or dispersoid is distributed such that a uniform apparent concentration of such substance, i.e. solute, dispersoid or reaction product thereof (which can be an analyte or an analyte precursor), is provided at the surface of the spreading layer facing the reagent layer(s) of the element. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The spreading layer advantageously produces a uniform apparent concentration of spread substance per unit area at its surface facing a reagent layer with which the spreading layer is in fluid contact. Such uniformity of apparent concentration can be determined by densitometric or other analytical techniques, such as is described in U.S. Pat. No. 3,992,158.

As mentioned herein, useful spreading or metering layers are desirably isotropically porous layers. Such layers can be prepared using a variety of components. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, etc., are desirable. Other desirable particles are diatomaceous earth and microcrystalline colloidal materials, e.g., microcrystalline cellulose, derived from natural or synthetic polymers. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, non-adherent particles can be coated with a thin adherent layer, such as a solution of hydrophilic colloid like gelatin or polyvinyl alcohol, and brought into mutual contact in a layer. When the colloid coating dries, the layer integrity is maintained and open spaces remain between its component particles.

As an alternative or in addition to such particulate materials, the spreading layer can be prepared using isotropically porous polymer compositions. It is possible to prepare such polymer compositions using techniques useful in forming blushed polymers, for example, as described in U.S. Pat. No. 3,555,129. Other techniques useful in preparing isotropically porous polymer compositions include those relating to the use of gas or other swellable constituents to create pores, as described in U.S. Pat. Nos. 2,960,728 and 2,946,095; or to the use within the polymer phase of a dissolvable solid that is dissolved to provide pores, for example, as discussed in U.S. Pat. No. 3,816,575.

Blushed (or precipitated) polymer layers are particularly desirable and can be formed on a substrate by dissolving a polymer in a mixture of two liquids, one of which is a lower boiling, good solvent for the polymer and the other of which is of a higher boiling point and is a non-solvent or a poor solvent for the polymer. Such a polymer solution is then coated on the substrate, and dried under controlled condition. The lower boiling solvent evaporates more readily and the coating can become enriched in the liquid which is a poor solvent or non-solvent. As evaporation proceeds, under proper conditions, the polymer forms as an isotropically porous layer. Many different polymers can be used, singly or in combination, for preparing isotropically porous blushed polymer spreading layers for use in this invention, typical examples being polycarbonates, polyamides, polyurethanes and cellulose esters such as cellulose acetate. Various microporous filters are, or are partly, blushed polymeric compositions, for example, various membrane filters of Millipore Corporation, and they have been described in patents such as U.S. Pat. No. 2,783,894 and U.S. Pat. No. 2,772,322.

Spreading layers can be prepared by coating from solution or dispersion. The range of materials useful for inclusion in any spreading layer is widely variable as discussed herein and will usually include predominantly materials that are resistant to, i.e., substantially insoluble in and non-swellable upon contact with water or other liquid under analysis. Swelling of about 10–14% of the layer's dry thickness may be normal. The thickness of the spreading layer is varible and will depend in part on the intended sample volume, which for convenience and cleanliness the spreading layer should be able to absorb, and on the layer's void volume, which also affects the amount of sample that can be absorbed into the layer. Spreading layers of from about 50 microns to about 300 microns dry thickness have been particularly useful. However, wider variations in thickness are acceptable and may be desirable for particular elements.

When preparing an isotropically porous spreading layer, it is useful to have void volume comprise at least about 25% of the total layer volume, and void volumes of from 50–95% may be desirable. Variations in void volume of porous spreading layers can be used advantageously to modify element characteristics as described in U.S. Pat. No. 3,992,158. It will be appreciated that the pore size in any case should be sufficient to permit spreading of initial sample components or other substances desirably provided to a reagent layer.

In preparing integral analytical elements of this invention, the layers can be preformed as separate layers which can thereafter be laminated prior to use or maintained as separate layers until brought into fluid contact when the element is in use. Layers preformed as separate members, if coatable, are typically coated from solution or dispersion on a surface from which the layer can be physically stripped when dried. However, a convenient procedure which can avoid problems of multiple stripping and lamination steps when contiguous layers are desired, is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well-known in the preparation of light-sensitive photographic films and papers. If it is essential or desirable that adjacent layers be discrete, and maintenance of layer separation by adjustment of coating formulation specific gravity is not satisfactory, as possibly in the case of porous spreading layers, the appropriate selection of components for each layer, including solvent or dispersion medium, can minimize or eliminate interlayer component migration and solvent effects, thereby promoting the formation of well-defined, discrete layers. Any interlayer adhesion problems can be overcome without harmful effect by means of surface treatments including extremely thin application of subbing materials such as are used in photographic films.

For coatable reagent layers, a coating solution or dispersion including the matrix and incorporated interactive materials can be prepared, coated as discussed herein and dried to form a dimensionally stable layer. The thickness of any reagent layer and its degree of permeability are widely variable and depend on actual usage. Dry thicknesses of from about 10 microns to about 100 microns have been convenient, although more widely varying thicknesses may be preferable in certain circumstances. For example, if comparatively large amounts of interactive material, e.g., polymeric materials like enzymes, are required, it may be desirable to use slightly thicker reagent layers. Fibrous reagent layers can be formed by impregnation of a fibrous matrix, in accordance with well-known techniques.

Radiation-blocking layers and registration layers can be prepared using methods and thicknesses as used when preparing coatable reagent layers, but with constituents appropriate for the particular layer. In the case of registration layers, in addition to their permeability and radiation-transmissiveness, they are desirably substantially free from any characteristic that might appear as or contribute to mottle or other noise in the detection of an analytical result produced in an integral element of the invention. For example, any variations in color or in texture within the registration layer, as could occur if fibrous materials, e.g., some papers, are used as a permeable medium, may be disadvantageous due to non-uniform reflectance or transmittance of detecting energy. This is also true regarding layers, e.g., radiation-blocking and reagent layers, of which at least the lower surace would be observable by a detection means examining a radiation-transmissive registration layer. Further, although fibrous materials like filter and other papers are generally permeable overall, some such materials typically can exhibit widely ranging degrees of permeability and may not exhibit uniform permeability, for example, based on structural variations such as fiber dimensions and spacing. As a result, such materials are not preferred in registration layers and other layers of elements of the present invention intended for quantitative analytical work.

As mentioned previously herein, the present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result direction. Preferred supports include radiation-transmissive support materials that transmit electromagnetic radiation of a wavelength or wavelengths within the region between about 200 nm and about 900 nm as well as radiation due to radioactivity. For fluorimetric detection of analytical results through the support, it is desirable for the support to transmit over a somewhat wider band than is necessary for non-fluorescence measurements, or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, the reagent layer, the radiation-blocking layer (if present) and the registration layer will usually be interposed in the element between the support and the spreading layer (if present), which often is the outermost layer in an element.

The components of any particular layer of an element of this invention, and the layer configuration of choice, will depend on the use for which an element is intended. As stated previously, spreading layer pore size can be chosen so that the layer can filter out undesirable sample components that would, for example, interfere with analytical reaction or with the detection of any test result produced within the element. For analysis of whole blood, porous layers having a pore size of from 1 to about 5 microns are particularly useful in screening out blood cells, which typically have a size of from about 7 to about 30 microns. If desirable, an element can include a plurality of spreading layers, each of which may be different in its ability to spread and filter. Also, if a restraint on transport of substances within the element additional to that provided by spreading layers is needed, a filter or dialysis layer can be included at an appropriate location in the element. As an example, in analyzing for blood glucose, a dialysis layer such as a semipermeable cellulose membrane can prevent passage of proteins or other potentially interfering substances to the reagent layer.

In the layers of the element, it can be advantageous to incorporate one or more surfactant materials such as anionic and nonionic surfactant materials. They can, for example, enhance coatability of layer formulations and enhance the extent and rate of spreading in spreading layers that are not easily wetted by liquid samples in the absence of an aid such as a surfactant. In particular it can be desirable to incorporate a surfactant, such as a non-ionic surfactant, in a spreading layer of the elements of the invention to normalize transport of the analyte contained in an aqueous proteinaceous liquid sample in and through this layer of the element. Such normalization refers to obtaining within the spreading layer an equivalent penetration of the solvent medium and dissolved components, including the analyte, of various applied samples of aqueous proteinaceous liquids, notwithstanding variations in protein concentration between such samples. Preferred amounts of surfactant effective to achieve normalized analyte transport are typically between about 1% and about 15% by weight based on the dry weight of the layer. Further details regarding this use of surfactant materials in the present invention may be found by reference to Goffe et. al., U.S. Pat. No. 4,050,898 issued Sept. 27, 1977.

In one or more of the various layers of the element, it may also be desirable, depending on the specific analyte of choice, to incorporate a buffer composition(s) to provide the appropriate pH for a particular assay. Typically, such a buffer composition can be incorporated into a reagent layer. However, such buffer compositions can also be incorporated in other layers such as the spreading layer, radiation-blocking layer, or registration layer. For example, phosphate buffers have been found useful in a reagent layer of an analytical element for the detection of $\alpha$-amylase. Of course, a variety of other pH buffer compositions are available and can be employed in the element of the invention. A partial listing of specific representative buffer compositions are described by Good in *Biochemistry*, 5, p. 467 (1966).

Analytical elements of the present invention can be adapted for use in carrying out a wide variety of chemical analyses, not only in the field of clinical chemistry but in chemical research and in chemical process control laboratories. They are well suited for use in clinical testing of body fluids, such as blood, blood serum and urine, since in this work a large number of repetitive tests are frequently conducted and test results are often needed a very short time after the sample is taken. In the field of blood analysis, for example, the multilayer element can be adapted for use in carrying out quantitative analyses for many of the blood components which are routinely measured. Thus, for example, the element may be readily adapted for use in the analysis of such blood components as albumin, bilirubin, $\alpha$-amylase, as well as many other components, by appropriate choice of test reagents or other interactive materials. In analyzing blood with the analytical element of this invention, the blood cells may first be separated from the serum, by such means as centrifuging, and the serum applied to the element. However, it is not necessary to make such separation, for example, if reflective spectrophotometric analysis techniques are used to quantify or otherwise analyze for the preformed detectable species in the element. Whole blood can be applied directly to the element and the blood cells filtered out and excluded from the registration layer through the action of a filtering layer, which can also be a radiation-blocking layer. The presence of these cells on the element will not interfere with spectrophotometric analysis if it is carried out by reflection techniques, with light being transmitted through the support and registration layer and reflected from the radiation-blocking layer or other reflecting layer such that detecting radiation does not intercept the cells. A particularly significant advantage of the integral analytical elements described herein is their ability to be used to analyze either serum or whole blood.

As can be appreciated, a variety of different elements, depending on the analysis of choice, can be prepared in accordance with the present invention. Elements can be configured in a variety of forms, including elongated tapes of any desired width, sheets or smaller chips. Particular elements can be adapted for one or more tests of a single layer or a variety of tests of different types. In such latter event, it can be desirable to coat a common support with one or more strips or channels, each optionally of a different composition to form a composite element suited for conducting a variety of desired tests.

The present elements are placed in use by applying to the element a sample of liquid under analysis. Typically, an element will be formed such that an applied sample will contact a spreading layer, if present, prior to a non-spreading reagent layer and will first contact such spreading layer at its surface farther from such reagent layer. Because analytical accuracy of the present elements is not substantially diminished by variations in the volume of applied samples, especially when a spreading layer is present in the element, sample application by hand or machine is acceptable. For reasons of convenience in detecting an analytical result, however, reasonable consistency in sample volume may be desirable.

In a typical analytical procedure using the present elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, if present, the element is exposed to any conditioning, such as heating, humidification or the like, that may be desirable to quicken or otherwise facilitate obtaining any test result. If an automated procedure is used, it can also be desirable to have any spreading layer accomplish its function within several seconds, but allowing sufficient time to provide metering, which is contrasted with the almost instantaneous, unregulated diffusion as can be obtained with absorbent fibrous papers. This can be accomplished conveniently by appropriate selection of various parameters, such as layer thickness, void volume in porous layers, etc.

After the analytical result is obtained as a detectable change, it is measured, usually by passing the element through a zone in which suitable apparatus for reflection, transmission or fluorescence spectrophotometry is provided. Such apparatus would serve to direct a beam of energy, such as light, through the support and the registration layer or the reagent layer. The light would then be reflected, such as from a radiation-blocking layer in the element, back to a detecting means or would pass through the element to a detector, in the case of transmission detection. Use of reflection spectrophotometry can be advantageous in some situations as it can effectively avoid interference from residues, such as blood cells, which may have been left on or in the layers of the element. Conventional techniques of fluorescence spectrophotometry can also be employed if the detectable species is a fluorescent material. Detection would be accomplished using energy that excites the fluorescent species and a detector that senses its fluorescent emission. Furthermore, when blood serum is tested or means are provided for eliminating unwanted whole blood residues, transmission techniques can be used to detect and quantify the indicating reaction products by directing a flow of radiant energy, for example, U.V., visible or I.R. radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the product produced in the element can be used. Various calibration techniques can be used to provide a control for the analysis. As one example, a sample of analyte standard solution can be applied adjacent to the area where the drop of sample is placed in order to permit the use of differential measurements in the analysis.

As a further illustration of the present invention, the following Examples are provided. These Examples are not exhaustive or limiting as to the scope of the invention, but are presented to provide detailed illustrations of certain specific embodiments of the invention.

EXAMPLE 1

Element Based on Dyed Starch for Assay of Amylase

An integral analytical element for the assay of α-amylase was prepared with the format shown in FIG. 2, containing in the spreading-reagent layer 6 as a light-soluble interactive composition a commercially available Amylochrome ® Starch purchased from Hoffman-LaRoche. This starch contains chemically bonded thereto as a preformed detectable moiety Cibachron ® Brilliant Blue F3GA dye, a reactive dye sold by Ciba-Geigy and based on cyanuric chloride. Also present in the reagent layer, as matrix, to assist spreading of the applied liquid sample to be assayed, were microcrystalline cellulose particles purchased from FMC Corporation under the name Avicel ®. The radiation-blocking layer 7 contained titanium dioxide particles in unhardened gel; the registration layer 4 contained a mordant (Mordant "A", poly[styrene-co-N-vinylbenzyl-,N-dimethylbenzylammonium chloride-co-divinyl benzene]), also in unhardened gel.

The element was prepared in the following manner:

A. Registration layer
  Water: 7.2 ml
  Unhardened gelatin (set mix of gel and water, 10% by weight gel): 10.6 g
  Mordant A, 13% by weight liquid mixture of mordant A in water: 8.2 ml
  p-nonylphenoxy glycerol, a surfactant commercially available as
  Surfactant 10G ® from Olin Mathieson Corp. (10% by weight solution of surfactant in water): 15 drops The gelatin was melted at 40° C. Water, mordant and surfactant were added and the melt was coated on a transparent polycarbonate support and air-dried.
Coverages:
  Gelatin: 2.16 g/m$^2$
  Mordant A: 2.16 g/m$^2$ B. Radiation-Blocking Layer
  1. TiO$_2$ Dispersion:
    Water: 160 ml
    TiO$_2$ particles: 40 g
    octylphenoxy polyethoxy ethanol, a surfactant commercially available as Triton ® X-100 from Rohm and Haas Company: 2 g Titanium dioxide was added to water and the mixture was thoroughly milled (colloid mill). Surfactant was then added.

2. Water: 11.0 ml
    TiO$^2$ dispersion (B1 above): 29.9 ml
    Unhardened gelatin (set mix of gel and water, 10% by weight of gel): 9.0 g The gelatin was melted at 40° C.; water and TiO$_2$ dispersion were mixed with light stirring (to prevent air entrapment), and coated over the aforementioned registration layer and air-dried.
Coverages:
  Gelatin: 3.65 g/m$^2$
  TiO$_2$: 24.30 g/m$^2$
  Triton ®X-100 surfactant: 1.22 g/m$^2$ C. Spreading-Reagent Layer
  Water: 24 ml
  Dye-containing starch (Amylochrome ® starch as identified above) purchased from Hoffman-LaRoche: ten 233 mg. tablets
  N-tris-hydroxymethyl(methyl-2-aminoethane-sulfonic acid) as a buffer: 65.5 mg
  Microcrystalline cellulose particles (Avicel ®): 2.5 g
  Surfactant 10G ® (10% by weight solution of surfactant in water): 0.5 ml The dye-containing starch tablets and buffer were lightly blended with water in a Waring Blendor ®. pH was adjusted to 7.0 with dilute sodium hydroxide. Microcrystalline cellulose particles were added and the mixture was blended again in a Waring Blendor ®. The surfactant was added with careful stirring to avoid entrapment of air. The mixture was coated and then dried.
Coverages:
  Dye-containing starch tablets: 215 tablets/m$^2$
  Microcrystalline cellulose: 54.0 g/m$^2$
  Buffer: 1.41 g/m$^2$ The above-described analytical element was then evaluated for amylase response in the following manner.

An amylase standard was prepared by diluting freshly donated human saliva 150 times with 1% albumin solution. The standard was assayed using Somogyi's method. [See N.W. Tietz, "Fundamentals of Clinical Chemistry", p. 412 (1970)]. A dilution series was generated from the standard by further dilutions with 1% albumin. The dilution series was applied to the element, and reaction proceeded at 42° C. during measurement.

Figure 7:
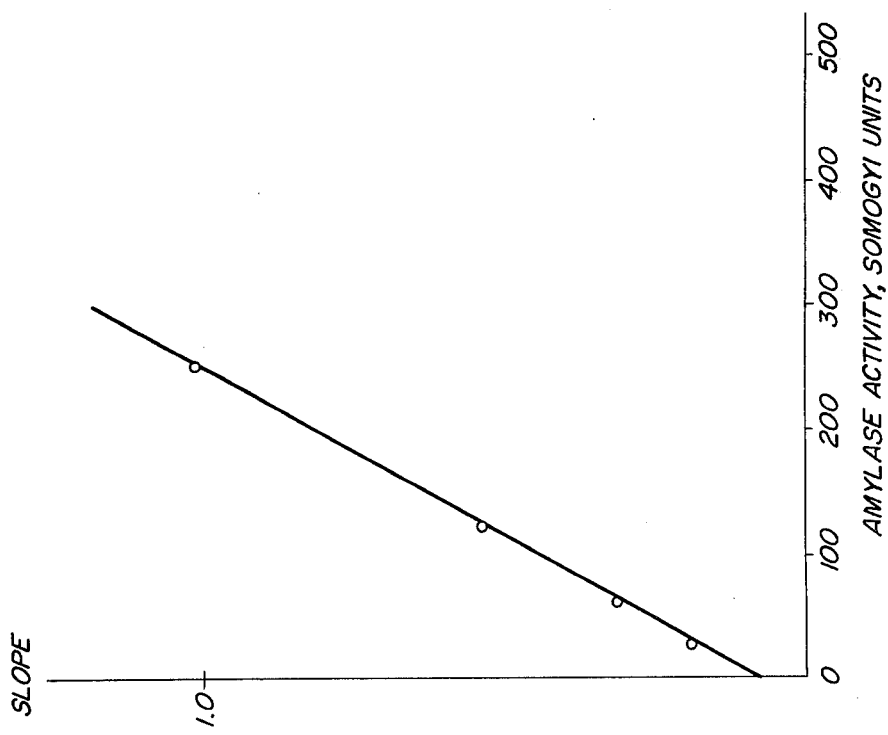

A colorimeter adapted for reflectance measurements on 16 mm. wide strips of a web consisting of the above-described analytical element was used, with a 620 nm. transmitting interference filter in front of the light source. Reflectance-vs.-time curves were recorded and converted to density-vs.-time curves. These density-vs.-time curves appear in FIG. 6; amylase levels in Somogyi units (SU) are indicated on each curve. At high amylase levels, these curves show a distinct straight line portion for several minutes, followed by a curvilinear region. The slope of the early part of the density-time curve was used as a measure of amylase activity. A plot of these initial slopes against amylase activity is shown in FIG. 7. The plot is linear up to about 300 Somogyi units, and the amylase assay based on the analytical element of this example is usable to about 500 Somogyi units.

EXAMPLE 2

Element Based on Fluorescent Labelled Starch

In this Example, an integral analytical element for the assay of amylase was prepared with the format shown in FIG. 2. In this element, the spreading-reagent layer contained as the interactive composition a starch having chemically bonded to repeating units of the starch polymer a preformed group which exhibits fluorescence upon reaction with starch.

A. Preparation of fluorescent labelled starch
 Potato starch: 30 g
 Isatoic anhydride: 5 g
 Pyridine: 5 ml
 Dimethyl sulfoxide: 130 ml The starch and isatoic anhydride were well mixed as dry powders. Dimethyl sulfoxide was added, and the mixture was heated to 50° C. with constant swirling. The pyridine was added, and the mixture was heated on a steambath overnight, protected from moisture. The very viscous solution was transferred into a Waring Blendor ®, and the starch was drowned out and washed by agitation in solvents with settling and decantation. For the washing, 500 ml each of acetone, methanol and acetone were used successively. The starch was filtered and air-dried. The yield was 33.1 g., a weight gain corresponding to about 75% utilization of isatoic anhydride. Analysis for nitrogen (Kjeldahl determination) gave 1.33% nitrogen, corresponding to about one anthranilate residue for six glucose residues of the starch polymer. (A second run of starch as described above gave a yield of 33.7 g corresponding to 90% utilization of isatoic anhydride. The nitrogen analysis for this run was 1.2 to 1.3%.)

B. Registration layer
 Water: 200 ml
 Agarose: 8.85 g
 Mordant A (See Ex. 1) 13% by weight liquid mixture of Mordant A in water: 13.6 ml
 Surfactant 10G ® (10% by weight solution of surfactant in water: 1.5 ml The agarose was dissolved in hot water, the mordant and surfactant were added and the mixture was coated on a transparent polycarbonate support and air-dried.

Coverages:
 Agarose: 5.40 g/m$^2$
 Mordant A: 1.08 g/m$^2$

C. Radiation-Blocking Layer
 Water: 50 ml
 Agarose: 796 mg

The agarose and water were heated until the agarose dissolved, thereby forming a first solution.
 Water: 19 ml
 NaCl: 398 mg
 Disodium phosphate: 796 mg
 Carbon black (15% by weight dispersion in water of Regal 300 ® carbon black manufactured by Cabot Co.): 5.3 ml
 Surfactant 10G ® (10% by weight solution of surfactant in water): 0.7 ml The above-noted salts (i.e., NaCl and disodium phosphate) were dissolved in 19 ml. of water to form a second solution, and the pH of the second solution was adjusted to 7.0 with dilute HCl. Carbon black and surfactant were added to the second solution; the second solution was added to the above-noted first solution; and the resultant mixture was coated over the aforementioned registration layer. The coating was air-dried.

Coverages:
 Agarose: 1.08 g/m$^2$
 Disodium phosphate: 1.08 g/m$^2$
 Carbon black: 0.54 g/m$^2$
 NaCl: 0.54 g/m$^2$ D. Spreading-Reagent Layer
 Water: 50 ml
 Fluorescent labelled potato starch: 2 g
 Microcrystalline cellulose: 8 g
 Surfactant 10G ® (10% by weight solution of surfactant in water): 10 drops The starch was dispersed in the above volume of water by sonication (Branson 185W Sonifier ®) at full power for 7 minutes, with an ice bath for external cooling. The dispersion was filtered through cheese cloth to remove undispersed slugs of polymer. The pH of the filtrate was adjusted to 7 with dilute potassium hydroxide. Microcrystalline cellulose was added, and the mixture was sonicated at half power for 3 minutes. Surfactant was carefully stirred in. The mixture was coated over the aforementioned radiation-blocking layer and the coating was air-dried.

Figure 9:
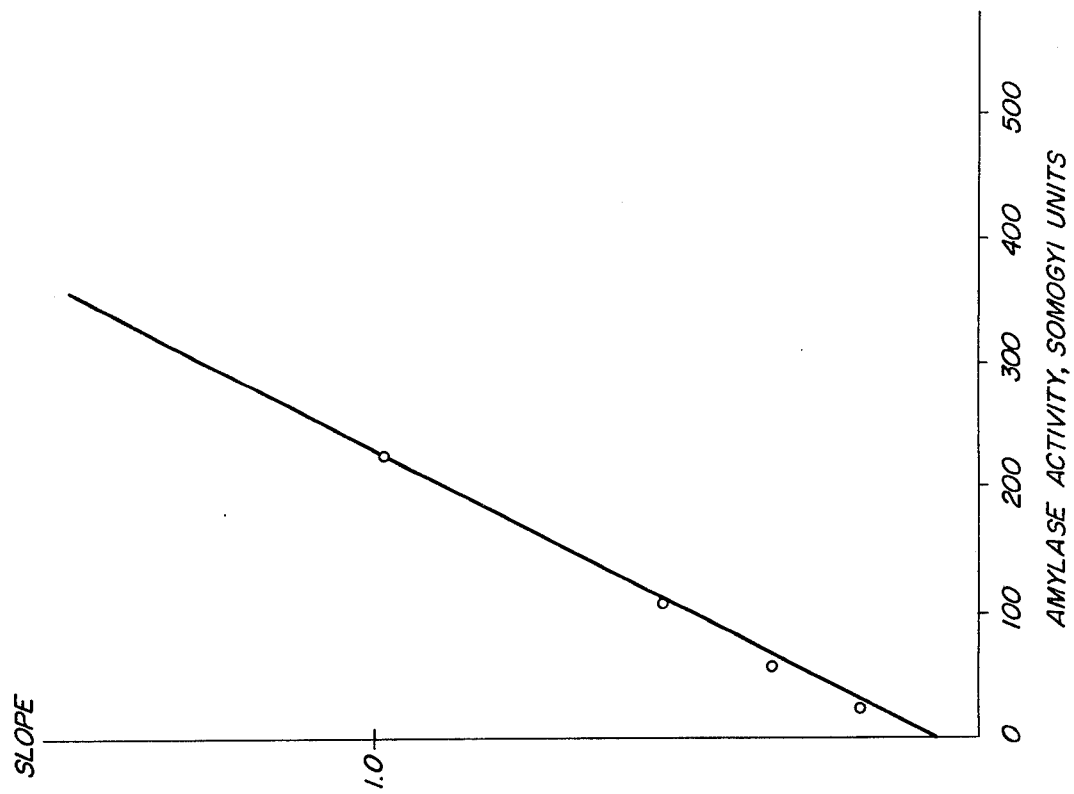
Figure 8:
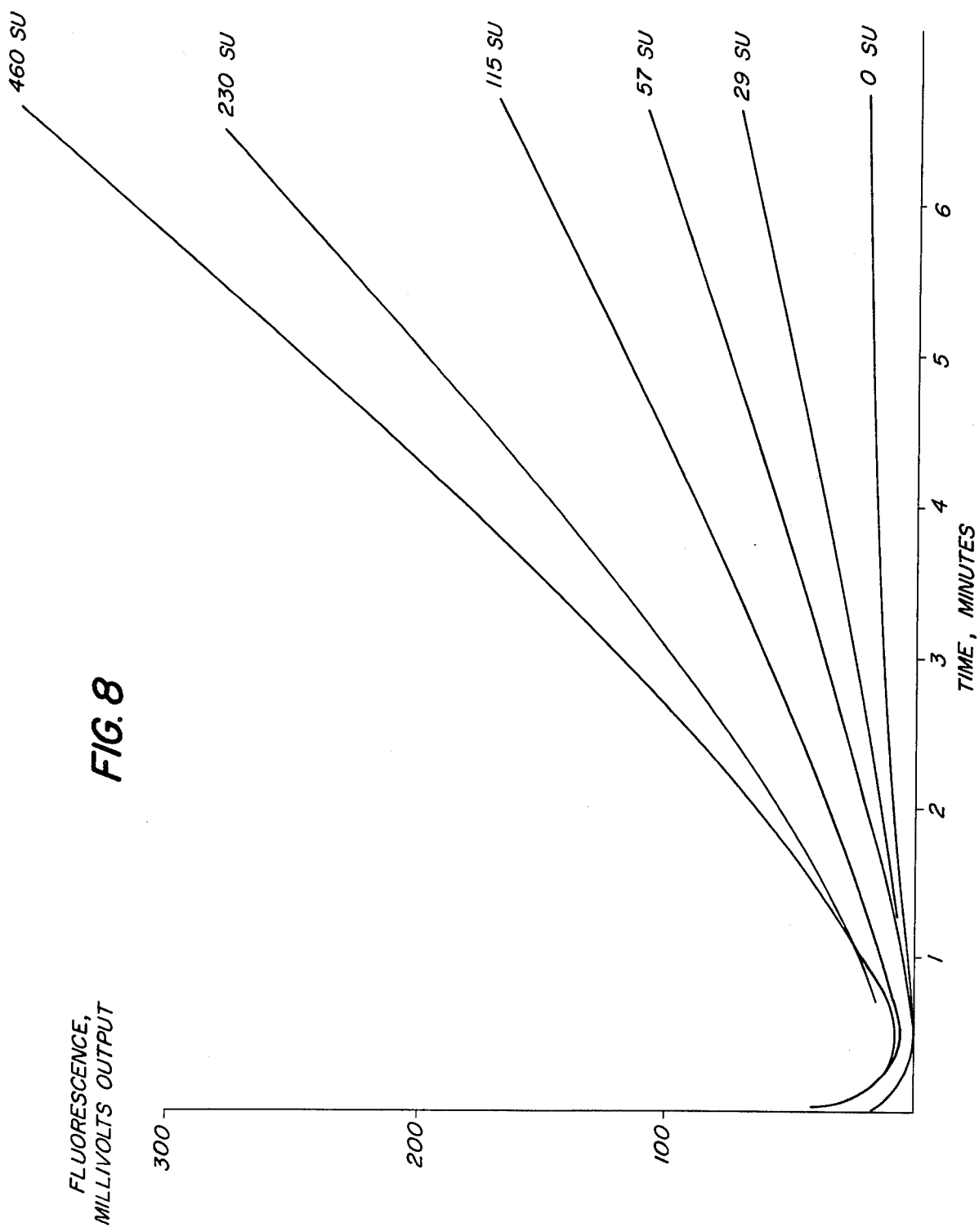

Coverages:
 Fluorescent labelled potato starch: 21.6 g/m$^2$
 Microcrystalline cellulose: 86.4 g/m$^2$ The above-described element was then evaluated for amylase response utilizing a standardized salivary amylase as described in Example 1. The change in fluorescence with time was monitored on a filtered fluorimeter, equipped with a Wratten ® 18A filter over the light source, and the results are shown in FIG. 8 for five levels of amylase plus a blank. The output curves in FIG. 8 are very nearly linear. Slopes of the output curves in FIG. 8 were measured at the five minute point. A plot of these slopes against amylase level was then prepared and is illustrated in FIG. 9. By happenstance, this slope plot is identical with that obtained with the dyed starch (FIG. 7). The fluorescent web exhibited adequate sensitivity to measure amylase at normal serum levels.

EXAMPLE 3

Element for Assay of Amylase

In this example, a further illustration of an integral analytical element for the assay of α-amylase is presented. The element of this example was prepared in a manner similar to that described in Example 1, except that the dyed starch of Example 1 was replaced with Amylopectin Azure A ®, a water-insoluble dyed starch purchased from Calbiochem, Los Angeles, California; the surfactant Triton X-100 ® used in the radiation-blocking layer of Example 1 was replaced by Surfactant 10G ®; the polycarbonate support of Example 1 was replaced by a transparent poly(ethylene terephthalate) support; the buffer used in the spreading-reagent layer of the element in Example 1 was deleted and, instead, the buffer sodium dihydrogen phosphate was used in the registration layer; and the amounts of various components contained in individual layers of the element were modified to improve coatability and element response. The individuals components and amounts thereof contained in each of the registration, radiation-blocking, and spreading-reagent layer of the element of this example were as follows:

| Registration Layer | Coating Coverage (g/m$^2$) |
| --- | --- |
| Unhardened gelatin | 5.4 |

| -continued | |
|---|---|
| Surfactant 10G ® | 0.65 |
| Sodium dihydrogen phosphate, pH 7.0 | 0.86 |
| Mordant "A" (See Example 1) | 2.1 |
| Radiation Blocking Layer | |
| Unhardened gelatin | 5.4 |
| Surfactant 10G ® | 0.3 |
| TiO$_2$ | 13. |
| Spreading-Reagent Layer | |
| Amylopectin Azure A ® | 21.5 |
| Microcrystalline cellulose | 64.5 |

The integral analytical element of this example was found effective in quantitatively establishing the α-amylase content of undiluted human serum samples over a range extending from 0 to about 1000 Somogyi units.

EXAMPLE 4

Element for Assay of Amylase

In this example, another illustration of an integral analytical element for the assay of α-amylase is illustrated. The analytical element of this example employed a water-soluble dyed starch, i.e., Dyamyl-L ® purchased from Warner-Lambert, rather than the insoluble dyed starch of Examples 1 and 3 above. In addition, the spreading-reagent system of this example, in contrast to Examples 1 and 3, was applied as a two-layer system in which the water-soluble dyed starch used in this Example was applied as a separate aqueous wash coating which inbibes into a previously-coated blushed polymer titanium dioxide particle-containing spreading layer. Also, in the element of this example agarose was used in place of the unhardened gel contained in the radiation-blocking and registration layer of Examples 1 and 3. The buffer, surfactants, and transparent web support employed in this example were identical to those of Example 3. The individual components and amounts thereof contained in the various layers of the element of this example were as follows:

| Registration Layer | Coating Coverage g/m.² |
|---|---|
| Mordant A (See Example 1) | 1.0 |
| Agarose | 2.0 |
| Surfactant 10G ® | .54 |
| Sodium dihydrogen phosphate, pH 7.0 | .86 |
| Radiation-Blocking Layer | |
| TiO$_2$ | 10.2 |
| Agarose | 1.0 |
| Surfactant 10G ® | .5 |
| Spreading-Reagent System | |
| A. Blushed polymer Spreading Layer | |
|     Cellulose acetate (∼40% acetylated) | 7.0 |
|     TiO$_2$ | 50.0 |
|     Polyoxyethylene (20) oleyl ether surfactant | 0.9 |
|     Triton X-405 ® surfactant purchased from Rohm and Haas | 1.4 |
|     Polyurethane elastomer, Estane ® Resin 5715 purchased from B.F. Goodrich | 1.5 |
| B. Water Soluble Dyed Starch Reagent Imbibed Into Spreading Layer | |
|     DyAmyl-L ® | 1.0 |

The integral analytical element of this example was found effective in quantitatively establishing the α-amylase content of undiluted human serum samples over a range extending from 0 to about 1000 Somogyi units.

EXAMPLE 5

Analytical Element For Bilirubin Assay

In this example, another embodiment of an integral analytical element of the present invention is illustrated. The element of this example is modified to be useful in bilirubin assay work and is specifically prepared to analyze for total bilirubin content contained in an aqueous liquid such as blood serum. The interactive composition contained in the reagent layer of this element is composed of a bilirubin-active complex and employs a competitive binding-displacement interaction which exists between bilirubin and the interactive composition. The bilirubin-active complex used in this example is composed of a preformed diffusible, bilirubin-displaceable detectable ligand bound to an albumin carrier which also can bind bilirubin. When a liquid sample containing bilirubin is contacted with the above-described bilirubin-active complex contained in the reagent layer of the element of this example, bilirubin binds to the albumin carrier of the complex and thus displaces the preformed detectable ligand which migrates to the registration layer of the element where its presence can be detected. The specific bilirubin assay and element of this example are the subject of Wu, U.S. Pat. No. 4,069,016 issued Jan. 17, 1978. Because certain aspects of the subject matter of the aforementioned patent represent a further specific embodiment of the present invention, it is included as a further example illustrating the scope of the present invention.

The multilayer analytical element of this example provides an effective element for the "dry" assay of bilirubin. Further details of such a bilirubin assay, if desired, may be found in the above-referenced Wu copending patent application hereby incorporated by reference. The multilayer element of this example was prepared as follows: In this example, a multilayer element was prepared having a cellulose acetate support, a polyvinyl alcohol (PVA) registration layer coated over the cellulose acetate base at a coverage of about 1.7 g/m² PVA to receive released detectable ligand from overcoated layers, a polymeric subbing layer coated over the polyvinyl alcohol registration layer, and a reagent layer containing a bilirubin-active complex composed of a 1:1 molar mixture of human serum albumin to the fluorescent probe ANS, i.e., 8-anilinonaphthalene-1-sulfonate, purchased from Eastman Organic Chemicals and having the formula

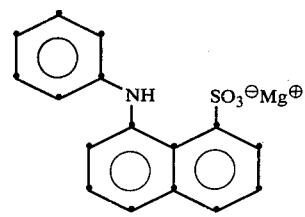

cellulose acetate, Triton X-100 ® (a nonionic octylphenoxy polyethoxyethanol surfactant sold by Rohm and Haas Co.), and titanium dioxide particles. In this reagent layer, the bilirubin-active complex was coated in an amount of about 5.4 g. of the complex per square meter, the cellulose acetate was coated in an amount of about 6.4 grams per square meter, the Triton X-100 ® surfactant was coated in an amount of about 1.4 grams per square meter, and the titanium dioxide particles were coated in an amount of about 49.5 grams per square meter. All coating coverages are based on dry weight of coated material excluding the weight of any liquid coating solvent. The reagent layer was coated from a solvent-non-solvent mixture to form a blush polymer layer. A series of sample test liquid solutions containing varying amounts of bilirubin ranging from 0 to about 50 milligrams of bilirubin per deciliter and also containing about 7 g/dl. of albumin was applied in 10 microliter sample drops to individual spots of the above-described multilayer element. As this was done, a Farrand MD-I spectrofluorometer purchased from Farrand Optical Co., Valhalla, N.Y., was used to measure the fluorescence both immediately before and 5 minutes after each bilirubin sample application. As a result, a calibration curve for bilirubin was generated and the resultant multilayer element was found capable of quantitatively evaluating known amounts of bilirubin in various sample solutions subsequently applied to this element which had been calibrated as described above. Each such bilirubin assay using this multilayer element could be performed in about 5 to 7 minutes. The presence of the albumin in the bilirubin sample solutions used to calibrate the analytical element did not appear to interfere with the response of the element to bilirubin. The spectrofluorometer was used to measure fluorescence of the reagent layer of the multilayer element of this Example by using an excitation wavelength of 396 nanometers and monitoring both this excitation wavelength and the emission wavelength maximum of ANS at 475 nanometers. The cellulose acetate base in this Example was selected because it exhibits little or no fluorescence to interfere with the measurements performed in this assay. Therefore, the fluorometric measurements could be made directly through the base of the above-described element. The fluorescence measurements clearly demonstrated a quasi-linear decrease in fluorescence exhibited by the bilirubin-active complex located in the reagent layer of the element as increasing amounts of bilirubin in the applied 10 microliter bilirubin-containing test samples were spotted onto the element, thereby indicating the bilirubin was competitively displacing the fluorescent probe ANS from the bilirubin-active complex. The fluorescent probe ANS in its free state exhibits little or no fluorescence, but, when bound to albumin, ANS is highly fluorescent.

EXAMPLE 6

Analytical Element For Glucose Assay

In this Example, another embodiment of an integral analytical element of the present invention is illustrated. The element of this Example was modified to be useful in glucose assay work. The interactive composition contained in the reagent layer of this element was composed of a ballasted, i.e., nondiffusible, dye-containing material which, upon undergoing a coupling reaction with an oxidized photographic developing agent, coupled off and released the dye.

More specifically, the multilayer element of this Example consisted of a polyethylene terphthalate support bearing, in order from the bottom to the top, a registration layer, a radiation-blocking layer, a reagent layer, and a spreading layer. The registration layer and radiation-blocking layers were substantially identical in composition to the layers of the same name used in the multilayer element of Example 1. The spreading layer of this Example was substantially identical to the blushed polymer spreading layer labelled "A" (of the Spreading-Reagent System) described hereinabove in Example 4. The reagent layer of this element was coated from aqueous solution and consisted of a hardened gel layer containing a ballasted dye-containing compound having formula 1:

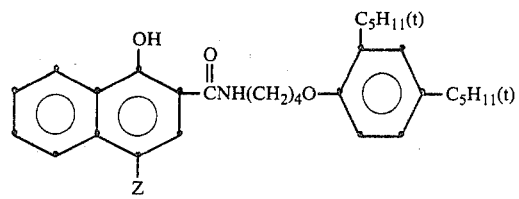

where Z is a pyridinium dye salt having formula 2:

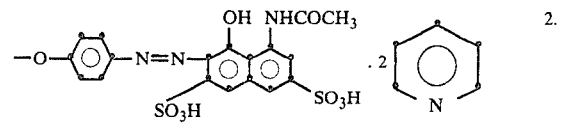

The reagent layer also contained a phosphate buffer, peroxidase (POD), glucose oxidase (GOD), aminoantipyrene (AAP), and a surfactant. In terms of coating coverage, the dry composition of the reagent layer was as follows:

Hardened gelatin: $20 g/m^2$
Compound formula 1 above: $4.4 g/M^2$
Phosphate buffer (pH 8.8) $10.1 g/m^2$
POD: 9500 units/$m^2$
GOD: 22700 units/$m^2$
Surfactant 10G ®: $0.4 g/m^2$
AAP: $0.8 g/m^2$ When the above-identified multilayer element was contacted by a small sample of human serum to which had been added GOD, the glucose analyte of the serum in the presence of the GOD (contained both in the serum sample and in the reagent layer) produced $H_2O_2$ which was converted to $O_2$ by the POD of the reagent layer. The $O_2$ oxidized the photographic developing agent AAP, which, in turn, interacted with the ballasted compound having formula 1 above the couple off and release the dye salt of formula 2 above. This released dye salt was diffusible and migrated to the registration layer as indicated by the visible color change detectable in the registration layer.

Although the invention has been described in considerable detail with particular reference to certain preferred embodiments thereof, variations and modifications can be effected within the spirit and scope of the invention.

I claim:

1. A multilayer analytical element for analysis of liquid containing a predetermined analyte, the element comprising a reagent layer and a registration layer,
   (a) said reagent layer comprising a composition including a non-diffusible material comprising a preformed, detectable moiety said composition being interactive in the presence of liquid containing said analyte to provide a diffusible species comprising the preformed, detectable moiety and
   (b) said registration layer adapted to receive said diffusible species,
   wherein layers within the element are composed such that said preformed, detectable moiety released from the reagent layer can be detected selectively within the element.

2. An analytical element as described in claim 1 wherein the registration layer is radiation-transparent.

3. An analytical element as described in claim 1 wherein the registration layer is at least as swellable in liquid under analysis as is the reagent layer.

4. An analytical element as described in claim 1 wherein the preformed, detectable moiety comprises a radiation emissive moiety or a colorimetrically detectable moiety.

5. An analytical element as described in claim 1 wherein said element comprises a radiation-transmissive support bearing said reagent layer and said registration layer.

6. A multilayer analytical element for analysis of liquid containing a predetermined analyte, the element comprising a support having superposed thereon a reagent layer and a registration layer,
   (a) said reagent layer comprising a composition including a non-diffusible material comprising a preformed, detectable moiety, said composition being interactive in the presence of liquid containing said analyte to provide a diffusible species comprising the preformed, detectable moiety, and
   (b) said registration layer adapted to receive said diffusible species,
wherein the registration layer is interposed between the reagent layer and the support and the reagent layer is removable from the registration layer, and wherein layers within the element are composed such that said preformed, detectable moiety can be selectively detected within the registration layer.

7. A multilayer analytical element for analysis of liquid containing a predetermined analyte, the element comprising a radiation-transmissive support having superposed thereon a reagent layer and a registration layer,
   (a) said reagent layer comprisingd a composition including a non-diffusible material comprising a preformed, detectable moiety, said composition being interactive in the presence of liquid containing said analyte to provide a diffusible species comprising the preformed detectable moiety, and
   (b) said registration layer adapted to receive said diffusible species,
wherein the registration layer is interposed between the support and the reagent layer and wherein the layers of the element are composed such that said preformed, detectable moiety can be selectively detected within the registration layer.

8. A multilayer analytical element for analysis of liquid containing a predetermined analyte, the element comprising a radiation-transmissive support having superposed thereon a reagent layer, a radiation-blocking layer, and a registration layer,
   (a) said reagent layer comprising a composition including a non-diffusible material comprising a preformed, detectable moiety, said composition being interactive in the presence of liquid containing analyte to provide a diffusible species comprising the detectable moiety, and
   (b) said radiation-blocking layer, permeable to the diffusible species, comprising an opacifying agent, and
   (c) said registration layer adapted to receive said diffusible species,
wherein the registration layer is the closest to the support of said layers and the radiation-blocking layer is interposed between the registration layer and the reagent layer, and wherein said preformed, detectable moiety can be selectively detected within the registration layer.

9. An analytical element as described in claim 8 wherein the opacifying agent comprises a pigment.

10. An analytical element as described in claim 8 wherein the opacifying agent comprises a reflective pigment.

11. An integral multilayer analytical element for analysis of liquid containing a predetermined analyte, the element comprising
   (a) an isotropically porous spreading layer comprising a non-fibrous material,
   (b) a reagent layer comprising a composition comprising a non-diffusable material including a preformed, detectable moiety, said composition being interactive in the presence of liquid containing said analyte to provide a diffusible product comprising the detectable moiety, and
   (c) a registration layer, permeable to the diffusible product, comprising a radiation-transmissive material,
wherein the reagent layer is interposed between the spreading layer and the registration layer, and wherein the preformed, detectable moiety can be detected selectively within the registration layer.

12. An integral multilayer analytical element for analysis of liquid containing a predetermined analyte, the element comprising
   (a) an isotropically porous spreading layer comprising a non-fibrous material,
   (b) a reagent layer comprising a composition comprising a non-diffusible material including a performed, detectable moiety, said composition being interactive in the presence of liquid containing said analyte to provide a diffusible product comprising the detectable moiety, and
   (c) a radiation-blocking layer, permeable to the diffusible product, comprising an opacifying agent,
   (d) a registration layer, permeable to the diffusible product, comprising a radiation-transmissive material,
wherein the reagent layer is interposed between the spreading layer and the radiation-blocking layer, and the radiation-blocking layer is interposed between the reagent layer and the registration layer, and wherein the preformed, detectable moiety can be detected selectively within the registration layer.

13. An analytical element as described in claim 11 wherein said element comprises a radiation-transmissive support, the registration layer being adjacent the support.

14. A multilayer analytical element for analysis of liquid containing a predetermined analyte, the element comprising
   (a) a porous reagent layer comprising a composition comprising a non-diffusable material including a preformed, detectable moiety, said composition being interactive in the presence of liquid containing said analyte to provide a diffusible product comprising the preformed, detectable moiety, and
   (b) a registration layer, permeable to the diffusible product, comprising a radiation-transmissive material,
wherein the preformed, detectable moiety can be detected selectively within the registration layer.

15. A multilayer analytical element for analysis of liquid containing a predetermined analyte, the element comprising,
   (a) a porous, reagent layer comprising a composition comprising a non-diffusible material including a preformed, detectable moiety, said composition being interactive in the presence of liquid containing said analyte to provide a diffusible product comprising the preformed, detectable moiety,
(b) a radiation-blocking layer, permeable to the diffusible product, comprising an opacifying agent, and
(c) a registration layer, permeable to the diffusible product, comprising a water-swellable, radiation-transmissive material.

wherein the radiation-blocking layer is interposed between the reagent layer and the registration layer, and wherein the preformed, detectable moiety can be detected selectively within the registration layer.

16. An analytical element as described in claim 15 wherein said element comprises a radiation-transmissive support, the registration layer being interposed between the support and the radiation-blocking layer.

17. A multilayer analytical element for analysis of liquid containing a predetermined analyte, the element comprising a radiation-transmissive support having thereon,
(a) a porous reagent layer comprising a composition comprising a non-diffusible material including a preformed, detectable moiety, said composition being interactive in the presence of liquid containing said analyte to provide a diffusible product comprising the preformed, detectable moiety,
(b) a radiation-blocking layer, substantially impermeable to said non-diffusible material and permeable to said diffusible product, comprising an opacifying agent, and
(c) a registration layer, permeable to the diffusible product, comprising a radiation-transmissive material, wherein the registration layer is adjacent the support and the radiation-blocking layer is interposed between the registration layer and the reagent layer, and wherein the preformed, detectable moiety can be detected selectively within the registration layer.

18. A multilayer analytical element for analysis of liquid containing a predetermined analyte, the element comprising,
(a) an isotropically porous reagent layer comprising a composition comprising a non-diffusible material including a preformed, detectable moiety, said composition being interactive in the presence of a liquid containing said analyte to provide a diffusible product comprising the preformed, detectable moiety, and
(b) a registration layer, permeable to the diffusible product, comprising a radiation-transmissive material, wherein the preformed, detectable moiety can be detected selectively within the registration layer.

19. An integral multilayer analytical element for analysis of liquid containing a predetermined analyte, the element comprising a radiation-transmissive support having thereon,
(a) an isotropically porous, non-fibrous reagent layer comprising a composition comprising a non-diffusible material including a preformed, detectable moiety, said composition being interactive in the presence of a liquid containing said analyte to provide a diffusible product comprising the preformed, detectable moiety,
(b) a radiation-blocking layer, permeable to the diffusible product, comprising an opacifying agent, and
(c) a registration layer, permeable to the diffusible product, comprising a radiation-transmissive material, wherein the registration layer is adjacent the support and the radiation-blocking layer is interposed between the reagent layer and the registration layer, and wherein the preformed, detectable moiety can be detected selectively within the registration layer.

20. An analytical element as described in claim 19 wherein the opacifying agent comprises a pigment.

21. An analytical element as described in claim 19 wherein the opacifying agent comprises a relfective pigment.

22. An analytical element as described in claim 19 wherein said preformed detectable moiety comprises a radiation-emissive moiety or a colorimetrically detectable moiety.

23. An analytical element as described in claim 19 wherein the registration layer comprises a hydrophilic colloid.

24. An integral multilayer element for analysis of liquid containing a predetermined analyte, the element comprising a radiation-transmissive support having thereon,
(a) an isotropically porous, non-fibrous reagent layer comprising a porous polymeric composition or particulate matter and a composition comprising a non-diffusible material including a preformed, detectable moiety, the latter said composition being interactive in the presence of liquid containing said analyte, to provide a diffusible product comprising the preformed, detectable moiety, and
(b) a registration layer, permeable to the diffusible product, comprising a radiation-transmissive material, wherein the registration layer is interposed between the support and the reagent layer and wherein the preformed, detectable moiety can be detected selectively within the registration layer.

25. An integral analytical element as described in claim 24 wherein said preformed detectable moiety comprises a radiation-emissive moiety or a colorimetrically detectable moiety.

26. An integral analytical element as described in claim 24 wherein the reagent layer includes a surfactant.

27. An integral analytical element as described in claim 24 wherein the reagent layer comprises particulate matter.

28. An integral analytical element as described in claim 24 wherein the reagent layer comprises particulate material selected from the group consisting of a microcrystalline colloid derived from a polymer, resinous beads and glass beads; and wherein the registration layer comprises a hydrophilic colloid.

29. An element as described in claim 24 wherein the reagent layer comprises microcrystalline cellulose particles and the registration layer comprises a hydrophilic colloid.

30. An element as described in claim 24 wherein the registration layer comprises a mordant for the diffusible product.

31. An integral analytical element as described in claim 24 wherein said element comprises a non-fibrous radiation-blocking layer, impermeable to said non-diffusible material and permeable to the diffusible product, comprising an opacifying agent, said radiation-blocking layer being interposed between the reagent layer and the registration layer.

32. An integral element as described in claim 31 wherein the opacifying agent comprises a pigment.

33. A multilayer analytical element for detecting amylase in liquids, the element comprising,
   (a) a reagent layer comprising a composition comprising a non-diffusible polysaccharide material including a preformed, detectable moiety, said composition being interactive in the presence of a liquid containing amylase to provide a diffusible moiety comprising the preformed, detectable moiety,
   (b) a registration layer, permeable to the diffusible product, comprising a radiation-transmissive material,
wherein layers within the element are composed such that said preformed, detectable moiety released from the reagent layer can be detected selectively within the element.

34. A multilayer analytical element as described in claim 33 wherein said element includes a radiation-blocking layer, permeable to the diffusible product, comprising an opacifying agent, said radiation-blocking layer being interposed between the reagent layer and the registration layer.

35. A multilayer analytical element as described in claim 33 wherein the non-diffusible polysaccharide material comprises starch having said detectable moiety chemically bonded thereto.

36. A multilayer integral analytical element as described in claim 33 wherein the detectable moiety comprises a colorimetrically detectable dye moiety or a fluorescent moiety.

37. A multilayer element for detecting amylase in liquids, the element comprising a radiation-transmissive support having thereon,
   (a) an isotropically porous reagent layer comprising a porous polymeric composition or particulate matter and a composition comprising a non-diffusible starch material including a preformed, detectable moiety, said composition being interactive in the presence of liquid containing amylase to provide a diffusible product comprising the preformed, detectable moiety,
   (b) a non-fibrous, radiation-blocking layer, permeable to the diffusible product, comprising an opacifying agent, and
   (c) a registration layer, permeable to the diffusible product, comprising a water-swellable, radiation-transmissive material,
wherein the registration layer is interposed between the support and the radiation-blocking layer and the radiation-blocking layer is interposed between the reagent layer and the registration layer, and wherein the preformed, detectable moiety can be detected selectively within the registration layer.

38. An analytical element as described in claim 37 wherein the isotropically porous reagent layer comprises the interactive composition and particulate matter comprising a microcrystalline colloid derived from a polymer.

39. An analytical element as described in claim 37 wherein the registration layer comprises a hydrophilic colloid selected from the group consisting of an acrylamide polymer, gelatin, agarose, dextran and a water-swellable polyvinyl compound.

40. An analytical element as described in claim 37 wherein the opacifying agent comprises a pigment selected from the group consisting of carbon, titanium dioxide, zinc oxide, lead oxide, and barium sulfate.

41. An integral multilayer analytical element for detecting amylase in liquids, the element comprising a radiation-transmissive support having thereon,
   (a) an isotropically porous reagent layer comprising particulate matter, a surfactant and a non-diffusible composition comprising starch having chemically bonded thereto a preformed, detectable moiety that is a colorimetrically detectable dye moiety or a fluorescent moiety, said starch being interactive in the presence of liquid containing amylase to provide a diffusible product comprising the preformed, detectable moiety,
   (b) a non-fibrous radiation-blocking layer, impermeable to said non-diffusible composition and permeable to the diffusible product, comprising a pigment, and
   (c) a registration layer, permeable to the diffusible product, comprising a hydrophilic colloid,
wherein the radiation-blocking layer is interposed between the registration layer and the isotropically porous reagent layer, wherein the registration layer is interposed between the support and the radiation-blocking layer, and wherein the preformed, detectable moiety can be detected selectively within the registration layer.

42. An integral analytical element as described in claim 41 wherein the registration layer comprises a mordant for the diffusible product.

43. An integral analytical element as described in claim 41 wherein the registration layer comprises a hydrophilic colloid selected from the group consisting of an acrylamide polymer, gelatin, agarose, dextran and a water-swellable polyvinyl compound.

44. An integral multilayer element for detecting amylase in liquids, the element comprising a radiation-transmissive support having thereon,
   (a) an isotropically porous reagent layer comprising particulate matter, a surfactant and non-diffusible starch having a dye moiety chemically bonded thereto, said starch being interactive in the presence of liquids containing amylase to provide a diffusible product comprising the dye moiety,
   (b) a non-fibrous, radiation-blocking layer, permeable to the diffusible product, comprising titanium dioxide and gelatin, and
   (c) a non-fibrous, radiation-transmissive registration layer comprising gelatin and poly-(styrene-co-N-vinylbenzyl-N,N-dimethylbenzyl-ammonium chloride-co-divinylbenzene),
wherein the registration layer is adjacent the support and the radiation-blocking layer is interposed between the reagent layer and the registration layer, and wherein the dye moiety can be detected selectively within the registration layer.

45. A method for detecting amylase in liquids, the method comprising the steps of
   (a) contacting a sample of liquid under analysis and a reagent layer of a multilayer analytical element comprising (i) said reagent layer and (ii) a registration layer, said reagent layer comprising a composition comprising a non-diffusible polysaccharide material including a preformed, detectable moiety, said composition being interactive in the presence of liquid containing amylase to provide a diffusible product comprising the preformed, detectable moiety, and said registration layer, permeable to the diffusible product, comprising a radiaton-transmissive material, wherein layers within the element are composed such that the preformed, detectable moiety released from the reagent layer can be detected selectively within the element, and
   (b) detecting, after a predetermined time, said preformed, detectable moiety.

* * * * *